(12) United States Patent
Rosen et al.

(10) Patent No.: US 7,217,845 B2
(45) Date of Patent: May 15, 2007

(54) BIFUNCTIONAL POLYETHYLENE GLYCOL DERIVATIVES

(75) Inventors: Perry Rosen, North Caldwell, NJ (US); Kwang Nho, Orinda, CA (US)

(73) Assignee: Sun Bio, Inc., Walnut Creek, CA (US)

( * ) Notice: Subject to any disclaimer, the term of this patent is extended or adjusted under 35 U.S.C. 154(b) by 614 days.

(21) Appl. No.: 10/721,013

(22) Filed: Nov. 21, 2003

(65) Prior Publication Data

US 2004/0115165 A1 Jun. 17, 2004

Related U.S. Application Data

(60) Provisional application No. 60/428,809, filed on Nov. 25, 2002.

(51) Int. Cl.
*C07C 47/00* (2006.01)
*C07C 233/00* (2006.01)
*C07C 235/00* (2006.01)
*C08F 283/00* (2006.01)

(52) U.S. Cl. ...................... 568/497; 564/192; 564/193; 564/197; 525/523

(58) Field of Classification Search ................. None
See application file for complete search history.

(56) References Cited

U.S. PATENT DOCUMENTS

| 4,528,334 | A | * | 7/1985 | Knopf et al. | ................ | 525/404 |
| 5,252,714 | A | * | 10/1993 | Harris et al. | ............. | 530/391.9 |
| 5,539,063 | A | * | 7/1996 | Hakimi et al. | .............. | 525/403 |
| 5,849,860 | A | * | 12/1998 | Hakimi et al. | .............. | 528/370 |
| 5,990,237 | A | * | 11/1999 | Bentley et al. | ............ | 525/54.2 |

* cited by examiner

*Primary Examiner*—Sikarl A. Witherspoon

(57) ABSTRACT

The present invention provides novel heterobifunctional and monobifunctional polyethylene glycol derivatives for the pegylation of therapeutically active proteins. The heterobifunctional PEGs which bear two different functional groups as well as the monobifunctional PEGs which contain two similar functional groups, may be used for cross-linking purposes. The cross-linking may be intramolecular between two areas within the same molecule or intermolecular between two separate molecules. The pegylated protein conjugates that are produced, retain a substantial portion of their therapeutic activity and are less immunogenic than the protein from which the conjugate is derived. New syntheses for preparing such bifunctional derivatives are described.

24 Claims, No Drawings

BIFUNCTIONAL POLYETHYLENE GLYCOL DERIVATIVES

CROSS REFERENCE TO RELATED APPLICATIONS

This Application claims priority of U.S. Provisional Ser. No. 60/428,809 filed Nov. 25, 2002, incorporated herein by reference.

BACKGROUND

Therapeutic proteins which are generally administered by intravenous injection may be immunogenic, relatively water insoluble, and may have a short in vivo half-life. The pharmacokinetics of the particular protein will govern both the efficacy and duration of effect of the drug. It has become of major importance therefore to reduce the rate of clearance of the protein so that prolonged action can be achieved. This can be accomplished by conjugation of a therapeutic polypeptide with a polymer such as polyethylene glycol (PEG). The effective molecular volume of the protein is thus increased and glomerular filtration is either avoided or inhibited (Brenner et al., (1978) Am. J. Physiol., 234, F455). By increasing the molecular volume and by masking potential epitope sites, modification of a therapeutic polypeptide with a polymer such as polyethylene glycol (PEG) has been shown to be efficacious in reducing both the rate of clearance as well as the antigenicity of the protein. Reduced proteolysis, increased water solubility, reduced renal clearance, and steric hindrance to receptor-mediated clearance are a number of mechanisms by which the attachment of a PEG polymer to the backbone of a polypeptide may prove beneficial in enhancing the pharmacokinetic properties of the drug. Thus Davis et al., U.S. Pat. No. 4,129,337 discloses conjugating PEG to proteins such as enzymes and insulin to produce a less immunogenic product while retaining a substantial proportion of the biological activity. PEG modification requires activation of the PEG polymer which is accomplished by the introduction of an electrophilic center. The PEG reagent is now susceptible to nucleophilic attack, predominantly by the nucleophilic epsilon-amino group of a lysyl residue or by a free sulfhydryl moiety when available. Because of the number of surface lysines present in most proteins, the pegylation process can result in random attachments leading to mixtures which are difficult to purify and which may not be desirable for pharmaceutical use. When however a free sulfhydryl group is available for conjugation, the pegylation process will result in the site specific introduction of the PEG polymer. There are a large variety of active PEGs which have been developed for the covalent modification of proteins via the formation of a linking group between PEG and protein (see for example Zalipsky, et al., and Harris et. al., in: Poly(ethylene glycol) Chemistry: Biotechnical and Biomedical Applications; (J. M. Harris ed.) Plenum Press: New York, 1992; Chap. 21 and 22). Some of these reagents however, are to various degrees, unstable in the aqueous medium in which the pegylation reaction occurs. In addition, the conjugation process often results in the loss of in vitro biological activity which is due to several factors foremost of which being a steric interaction with the protein's active sites. A desired property therefore of a new pegylating reagent would be one that is not susceptible to rapid degradation in an aqueous medium and one which may be employed to affect the site specific modification of a protein. Cross-linking derivatives such as a PEG dialdehyde and a PEG polymer which has an aldehyde function at the alpha position and a sulfydryl specific group at the omega position may be considered as such reagents. For site specific N-terminal reductive amination, see Pepinsky et al., (2001) JPET, 297, 1059 (Interferon-•-1a) and U.S. Pat. No. 5,824,784 (1998) to Kinstler et al., (G-CSF). The use of a PEG-aldehyde for the reductive amination of a protein utilizing other available nucleophilic amino groups, is described in U.S. Pat. No. 4,002,531 (1977) to Royer, in EPO 154 316, by Wieder et al., (1979) J. Biol. Chem. 254, 12579, and Chamow et al., (1994) Bioconjugate Chem. 5, 133. For the site specific pegylation of a protein via a free sulfhydryl group see Goodson et al., Bio/Technology (1990) 8, 343.

As in the case of pegylation with monofunctional PEG reagents, the cross-linking of proteins with a PEG polymer may be employed to enhance the stability of the protein as well as increase the effective molecular volume of those proteins that may otherwise be susceptible to glomerular filtration and therefore rapid clearance from the circulation. Cross-linking reagents have been found in general to have the same type and degree of reactivity as the analogous monofunctional reagent although the length and flexibility of the cross-link may vary greatly. Cross-linking may involve the coupling of two similar or diverse molecular components such as proteins, peptides, or pharmaceuticals which can provide in a single molecular entity two different activities (see for example Saleh et al., (2000) J. Clin. Oncol. 18, 2282).

An example of intramolecular cross-linking is described in the case of hemoglobin, where the cross-bridging process has been used in an attempt to prevent the dissociation of the tetramers into their constituent •,• dimers (Zhang et al. (1989) Biochem. Biophys. Res. Commun. 163, 733; Manjula et al. (2000) J. Biol. Chem. 275, 5527).

SUMMARY OF INVENTION

In accordance with this invention, it has been discovered that aldehydes of the formula:

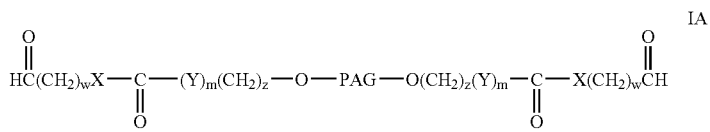

IA wherein X and Y are individually selected from —O— or —NH— with the proviso that X is NH when m is 1 and Y is —O—, PAG is a divalent residue of polyalkylene glycol resulting from removal of the terminal hydroxy groups and having a molecular weight of from 500 to 100,000 Daltons, z is an integer of from 2 to 4, m is an integer of from 0 to 1, and w is an integer of from 2 to 8;

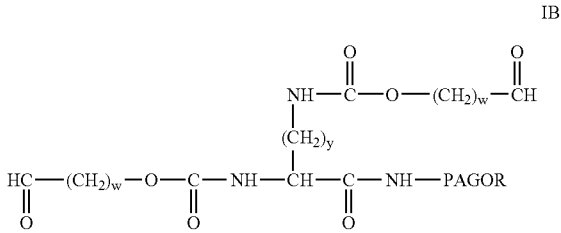

IB wherein R is hydrogen or lower alkyl, PAG is a divalent residue of polyalkylene glycol resulting from removal of the terminal hydroxy groups and having a molecular weight of from 500 to 100,000 Daltons, w is an integer of from 2 to 8, and y is an integer of from 2 to 4;

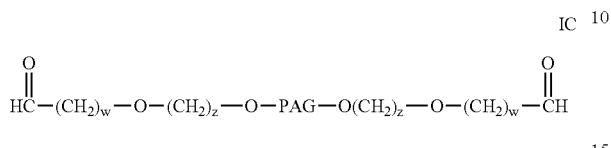

IC wherein PAG and z are as above, and w is an integer of from 2 to 8;

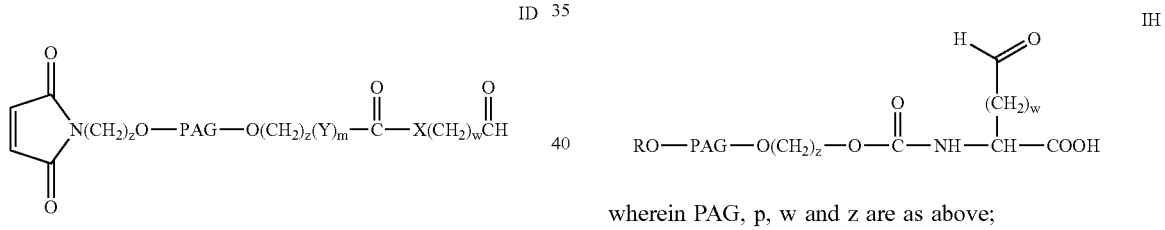

ID wherein X and Y are individually selected from —O— or —NH— with the proviso that X is NH when m is 1 and Y is —O—, PAG is a divalent residue of polyalkylene glycol resulting from removal of the terminal hydroxy groups and having a molecular weight of from 500 to 100,000 Daltons, z is an integer of from 2 to 4, m is an integer of from 0 to 1, and w is an integer of from 2 to 8;

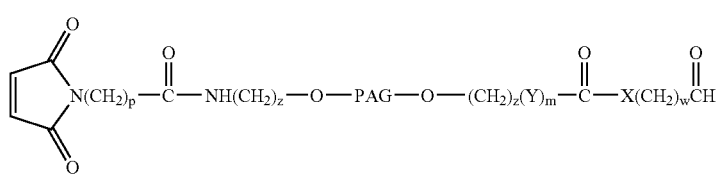

IE wherein X and Y are individually selected from —O— or —NH— with the proviso that X is NH when m is 1 and Y is —O—, PAG is a divalent residue of polyalkylene glycol resulting from removal of the terminal hydroxy groups and having a molecular weight of from 500 to 100,000 Daltons, z is an integer of from 2 to 4, m is an integer of from 0 to 1, p is an integer of from 1 to 10, and w is an integer of from 2 to 8;

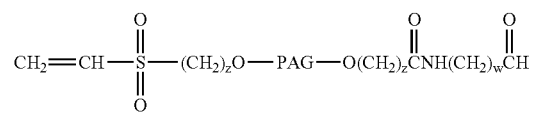

IF wherein PAG is a divalent residue of polyalkylene glycol resulting from removal of the terminal hydroxy groups and having a molecular weight of from 500 to 100,000 Daltons, and w and z are as above;

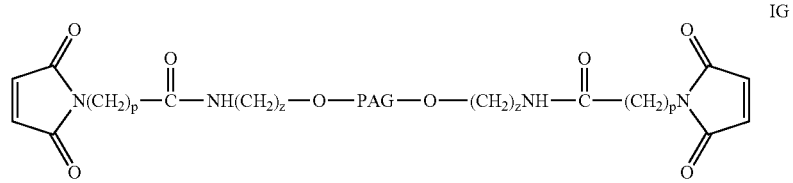

IG wherein PAG, p and z are as above;

IH wherein PAG, p, w and z are as above;

are useful for cross-linking to therapeutically active agents such as proteins, peptides and pharmaceuticals to produce PEG conjugates which retain a substantial portion of the therapeutic activity of these agents. These conjugates have an enhanced in vivo half-life and are less immunogenic than the agents from which these conjugate are derived.

DETAILED DESCRIPTION

The homobifunctional reagents of formula IA, IB, and IC are dialdehydes which can be used in a cross-linking reaction via a reductive amination reaction by conjugation at a proteins terminal amino acid or at the, -amino group of a lysine residue. The cross-linking may be intramolecular between two areas within the same molecule or intermolecular between two separate molecules. The heterobifunctional reagents of formula ID, IE IF, and IH contain two distinct functional groups with different specificities. One end of the cross-linker in ID, IE, and IF is selective for a sulfhydryl group while the aldehyde at the other end is directed to amino groups. In IH, both functional groups will react with an amine but at much different rates of reaction. Because of the large differences in reactivity of the two functional groups found in compounds ID, IE, IF, and IH the sequence of steps in the cross-linking reaction can be well controlled and the product that is obtained is a result of site selectivity. If the product is formed by an intermolecular mechanism, it will necessitate the use of two different proteins, each being incorporated by reacting at a particular terminus of the same polymer chain. To form an intramolecular cross-linked product, one mole of reagent is reacted with one mole protein, said protein having on its surface both amino and sulfhydryl functional groups. Compounds IA, IB, and IC possess only aldehyde linkers which are selective for amino groups. These reagents will induce a reaction with two moles of the same protein to give a product in which each protein is attached to one end of the polymer chain. Intramolecular cross-linking is induced between two amino groups both of which are found within a single locale. The homobifunctional reagent 1G has been designed to induce cross-bridging between two molecules of the same protein in which there is a reactive sulfhydryl functional group, and intramolecularly cross-linking with one mole of a polypeptide which has at least two sulfhydryl groups present in its amino acid sequence.

The cross-linking reagents herein described contain stable linkages that do not react rapidly with water under physiological conditions. They can be conjugated to therapeutically active proteins to produce therapeutically active protein conjugates that retain a substantial portion of the biological activity of the proteins from which they are derived. In addition, the reagents of this invention are not susceptible to rapid degradation in the aqueous medium in which the pegylation reaction is carried out. Furthermore, the reagents of this invention can be cross-linked to proteins in a controlled manner at the N-terminus and at a specific sulfhydryl group. In this way, these regents produce the desired conjugates and avoid random attachments, which can lead to mixtures which are difficult to purify and which may not be desirable for pharmaceutical use. This is extremely advantageous since extensive purification procedures may bring about an irreversible change in the proteins tertiary structure and therefore its therapeutic usefulness.

The therapeutic proteins, which can be cross-linked in accordance with this invention, can be any of the conventional therapeutic proteins or mutants thereof, peptides and pharmaceuticals. Among the preferred proteins are included interferon-alpha, interferon-beta, consensus interferon, G-CSF, GM-CSF, EPO, hemoglobin, interleukins, colony stimulating factor, as well as immunoglobulins such as IgG, IgE, IgM, IgA, IgD and fragments thereof.

The term polyalkylene glycol designates poly (lower alkylene) glycol radicals where the alkylene radical is a straight or branched chain radical containing from 2 to 7 carbon atoms. The term "lower alkylene" designates a straight or branched chain divalent alkylene radical containing from 2 to 7 carbon atoms such as polyethylene, polypropylene, poly n-butylene, and polyisobutylene as well as polyalkylene glycols formed from mixed alkylene glycols such as polymers containing a mixture of polyethylene and polypropylene radicals and polymers containing a mixture of polyisopropylene, polyethylene and polyisobutylene radicals. The branched chain alkylene glycol radicals provide the lower alkyl groups in the polymer chain of from 2 to 4 carbon atoms depending on the number of carbon atoms contained in the straight chain of the alkylene group so that the total number of carbons atoms of any alkylene moiety which makes up the polyalkylene glycol substituent is from 2 to 7. The term "lower alkyl" includes lower alkyl groups containing from 1 to 7 carbon atoms, preferably from 1 to 4 carbon atoms, such as methyl, ethyl, propyl, isopropyl, etc. with methyl being especially preferred.

In accordance with a preferred embodiment of this invention, PAG in the compound in formulas IA, IB, IC, ID, IE, IF, 1G, and IH is a polyethylene glycol residue formed by removal of the two terminal hydroxy groups and which has a molecular weight of from about 500 to 100,000. However good results are also achieved when the polyethylene glycol residue has a molecular weight of from 1,000 to 100,000 preferably from about 5,000 to 50,000. Most preferably from 20,000 to 40,000. The reagents exemplified by the compounds of formula IA, IB, IC, ID, IE, IF, 1G, and IH are used in forming polyalkyleneoxy protein conjugates. The aldehydes present in the cross-linking agents of this invention are intermediates for conjugation with the terminal amino group as well as with other free amino groups on the protein. The maleimido function found in compounds ID, IE and 1G and the vinyl sulfone in compound IF are thiol specific reagents. These reagents may be used to produce therapeutically effective conjugates in which the proteins that have been cross-linked, have the same curative properties as the native protein. Furthermore, the conjugates are more soluble in water and show a reduced rate of clearance and a decreased antigenicity as compared to that of the starting protein. These properties make them more effective therapeutic agents than the unmodified protein. The aldehydes of this invention may react with an amino group of a protein to form a PEG-protein conjugate in accordance with the following scheme:

Scheme 1

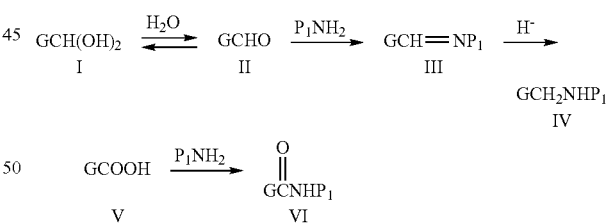

wherein $P_1NH_2$ is a protein covalently attached to a PEG via a nucleophilic amino group.

In Scheme 1, GCHO in the compound of formula II and GCOOH in the compound of formula IIa are a composite of the compounds of IA, IB, IC, ID, IE, IF, and IH showing the reactive aldehyde and carboxyl groups. In this reaction scheme, $P_1NH_2$ is the protein containing a nucleophilic —$NH_2$ group that is conjugated with the compounds of formula IA, IB, IC, ID, IE, IF, and IH.

As shown in the above reaction scheme, an equilibrium may be established in aqueous medium between the aldehyde II and its hydrate I. The composition of this equilibrium i.e., the concentration of the hydrate I, is dependant on the pH of the solution and the structure of the particular aldehyde II. The Schiff base III is formed by the condensation the polyalkylene aldehyde of formula II with a protein amine $P_1NH_2$. Reduction of the imine linkage of formula III with an agent such as cyanoborohydride, affords the saturated conjugated protein of formula IV. The reaction whereby aldehydes are conjugated with proteins through reductive amination is set forth in U.S. Pat. No. 4,002,531, EPO 154,316 and U.S. Pat. No. 5,824,784. The reaction whereby a PEG acid such as IIa is conjugated with a protein to give an amide derivative such as IVa, is set forth in U.S. Pat. No. 5,824,784.

Each of the aldehyde functional groups represented in formulas IA, IB, IC, ID, IE, IF, and IH may react preferentially with $P_1NH_2$ at a single site located at the N-terminus amine on the protein. This can be done by carrying out the reductive amination reaction at a pH of from 5.5 to 7.5. In carrying out this reaction, various buffers which maintain the reaction media at a pH of from 5.5 to 7.5 can be used. Unlike the N-terminus, the reductive amination of the 0-amino groups of the lysine residues in the polypeptide backbone requires a pH of 8.0 and above, preferably a pH of from 8 to 10. In this manner, amino groups, as well as the N-terminal amino group on the protein may be reductively aminated with the PAG aldehydes of this invention.

The maleimido reagents of this invention may react with a sulfhydryl group of a protein to form a PEG-protein conjugate in accordance with the following scheme:

Scheme 2

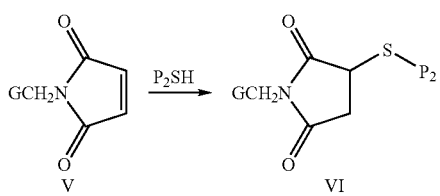

wherein $P_2SH$ is a protein which can be covalently and selectively attached to a maleimidyl PEG derivative.

In Scheme 2, $G$-$C_5H_4NO_2$ in the compound of formula V is a composite of the compounds of ID, IE and 1G showing the reactive maleimido group. $P_2SH$ is the protein containing a nucleophilic —SH group that is conjugated with the compounds of formula ID, IE and 1G to form a thioether which is exemplified by compound VI.

In Scheme 3, $G$-$C_3H_5SO_2$ in the compound of formula VII is a composite of the compound of IF showing the reactive vinyl sulfone group. $P_2SH$ is the protein containing a nucleophilic —SH group which is conjugated with the compounds of formula VII to form a Michael addition product which is exemplified by compound VIII and shown in the following scheme:

Scheme 3

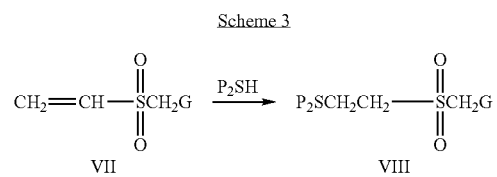

wherein $P_2SH$ is a protein which can be covalently and selectively attached to a sulfone PEG derivative.

Exemplary sulfhydryl coupling agents are the maleimido groups which are found in compounds ID, IE and 1G. These agents are specific to sulfhydryl groups, particularly at a pH below 7. The covalent attachment of these sulfhydryl coupling agents to a cysteine residue is via a thioether linkage generated by the reaction of the thiol moiety with a maleimide group found in compounds ID, IE and 1G (Scheme 2). The selective derivatization of a sulfhydryl group of a cystein amino acid is made possible by the reactivity of sulfhydryl specific reagents which can form covalent bonds with the cysteine residues at a rate which is approximately 1000 times faster than the reaction with a corresponding amine. Furthermore, the Michael reaction product VI is quite stable and is not cleaved under physiological conditions (Wong, S. S., Chemistry of Protein Conjugation and Cross-Linking, CRC Press, Boca Ratan, 1993, 30). Similarly the vinyl sulfone of compound VII in Scheme 3, is selective for reaction with a sulfhydryl group as compared to a corresponding amine. For examples of pegylation of proteins with PEG-maleimide reagents see Goodson et al., (1990) Bio/Technology, 8, 343–346 and Shaw et al., U.S. Pat. No. 5,166,322. For use of a PEG vinyl sulfone as a sulfhydryl specific reagent, see Morpurgo et al. (1996) Bioconjugate Chem. 7, 363.

The specific pegylating reagents of formula IA, IB, IC, and IH of this invention, are stable in aqueous medium and not subject to rapid aldol decompositions under the conditions of the reductive amination reaction. The amino groups on proteins such as those on the lysine residues are the predominate nucleophilic centers for the condensation of the aldehydes of this invention. However by controlling the pH of the reaction one can produce a site specific introduction of a polyalkylene glycol polymer on the protein at the desired N-terminus amino acid. When the compounds of formula IA are conjugated to a protein as is shown in Scheme 1, by an intermolecular mechanism, the resulting compound is IIA,

IIA

wherein $P_1$ is a residue of a protein resulting from removal of a primary amino group, and where Y, PAG, X, m, w and z are as above.

When the compounds of formula IA are conjugated to a protein as is shown in Scheme 1, by an intramolecular mechanism, the resulting compound is IIAA,

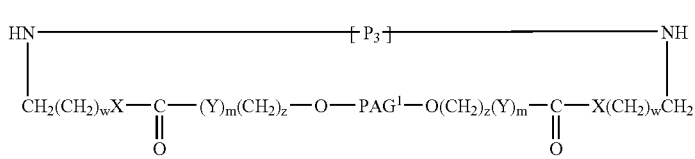

IIAA wherein Y, X, m, w and z are as above and [$P_3$] is the divalent residue of a protein resulting from removal of two primary amino groups, $PAG^1$ is a polyethylene glycol residue formed by removal of the two terminal hydroxy groups and having a molecular weight of from about 500 to 20,000.

When the compounds of formula IB are conjugated to a protein as is shown in Scheme 1, by an intermolecular mechanism, the resulting compound is IIB,

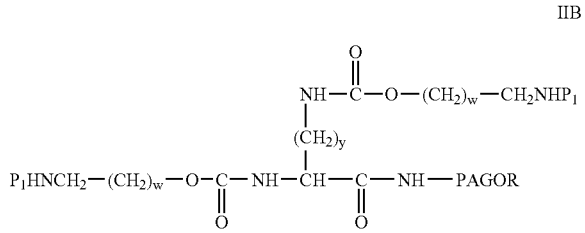

IIB wherein, $P_1$ is as above, R is hydrogen or lower alkyl, PAG is a divalent residue of polyalkylene glycol resulting from removal of the terminal hydroxy groups and having a molecular weight of from 500 to 100,000 Daltons, w is an integer of from 2 to 8, and y is an integer of from 2 to 4.

When the compounds of formula IB are conjugated to a protein as is shown in Scheme 1, by an intramolecular mechanism, the resulting compound is IIBB,

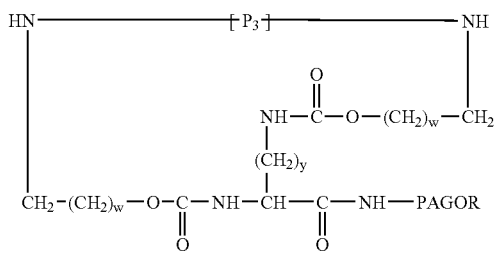

IIBB wherein, R is hydrogen or lower alkyl, PAG is a divalent residue of polyalkylene glycol resulting from removal of the terminal hydroxy groups and having a molecular weight of from 500 to 100,000 Daltons, w is an integer of from 2 to 8, y is an integer of from 2 to 4, and [$P_3$] is the divalent residue of a protein resulting from removal of two primary amino groups.

When the compounds of formula IC are conjugated to a protein as is shown in Scheme 1, by an intermolecular mechanism, the resulting compound is IIC,

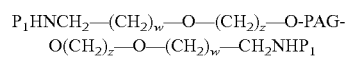

IIC wherein $P_1$, PAG, and z are as above, and w is an integer of from 2 to 8.

When the compounds of formula IC are conjugated to a protein as is shown in Scheme 1, by an intramolecular mechanism, the resulting compound is IICC,

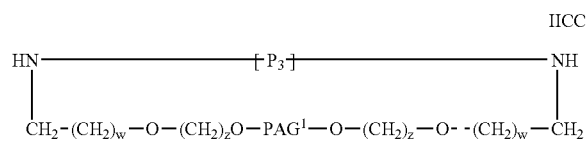

IICC wherein [$P_3$], $PAG^1$, and z are as above, and w is an integer of from 2 to 8.

When the compounds of formula ID are conjugated to a protein as is shown in Scheme 1 and Scheme 2, by an intermolecular mechanism, the resulting compound is IID,

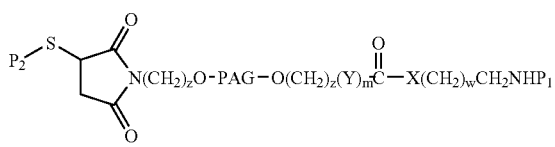

IID wherein $P_2$ is the residue of a protein resulting from removal of a sulfhydryl group, $P_1$ is as above, X and Y are individually selected from —O— or —NH— with the proviso that X is NH when m is 1 and Y is —O—, PAG is a divalent residue of polyalkylene glycol resulting from removal of the terminal hydroxy groups and having a molecular weight of from 500 to 100,000 Daltons, z is an integer of from 2 to 4, m is an integer of from 0 to 1, and w is an integer of from 2 to 8.

When the compounds of formula ID are conjugated to a protein as is shown in Scheme 1 and Scheme 2, by an intramolecular mechanism, the resulting compound is IIDD,

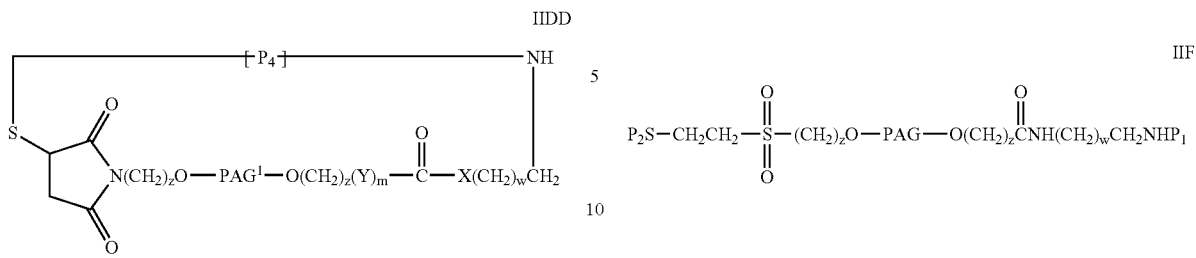

wherein PAG¹, X, Y, m, w, z are as above, [P₄] is the divalent residue of a protein resulting from removal of a primary amino group and a sulfhydryl group.

When the compounds of formula IE are conjugated to a protein as is shown in Scheme 1 and Scheme 2, by an intermolecular mechanism, the resulting compound is IIE,

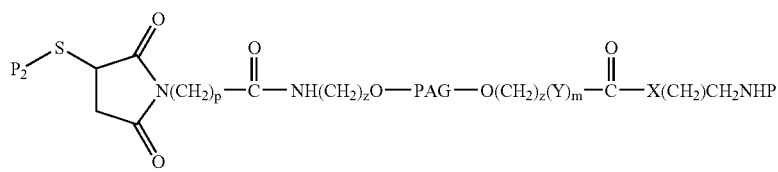

wherein P₂, P₁, X, Y, PAG, m, w, and z are as above, and p is an integer of from 1 to 10.

When the compounds of formula IE are conjugated to a protein as is shown in Scheme 1 and Scheme 2, by an intramolecular mechanism, the resulting compound is IIEE,

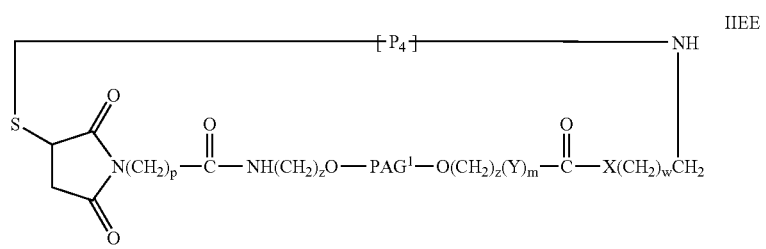

wherein X, Y, PAG¹, m, w, z, p and [P₄] are as above.

When the compounds of formula IF are conjugated to a protein as is shown in Scheme 1 and Scheme 3, by an intermolecular mechanism, the resulting compound is IIF,

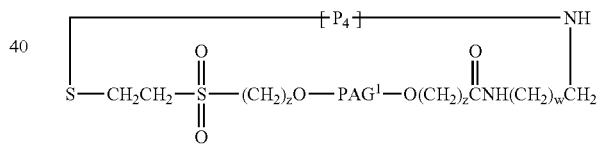

wherein P₁, P₂, PAG, w and z are as above.

When the compounds of formula IF are conjugated to a protein as is shown in Scheme 1 and Scheme 3, by an intramolecular mechanism, the resulting compound is IIFF, wherein [P₄], PAG¹ z and w are as above.

When the compounds of formula IG are conjugated to a protein as is shown in Scheme 2, by an intermolecular mechanism, the resulting compound is IIG,

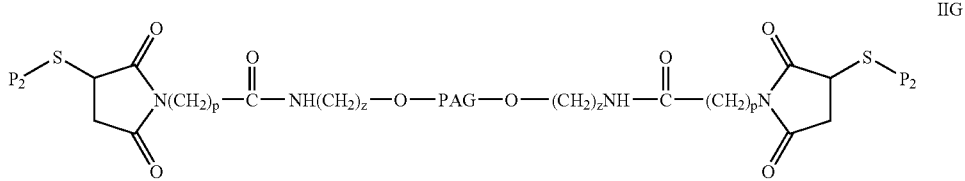
IIG wherein PAG, p and z are as above, and $P_2$ is the residue of a protein resulting from removal of a sulfhydryl group.

When the compounds of formula IG are conjugated to a protein as is shown in Scheme 2, by an intramolecular mechanism, the resulting compound is IIGG, wherein PAG, z and w are as above. $P_1$ and $P_6$ are the residues of two proteins, each resulting from removal of a primary amino group.

In accordance with this invention, in formula IA, when m is 0 and X is —NH—, these compounds have the formula:

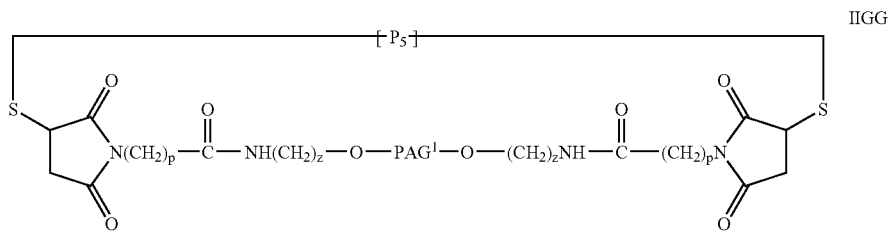
IIGG wherein $PAG^1$, p and z are as above, and $[P_5]$ is the divalent residue of a protein resulting from removal of two sulfhydryl groups.

When the compounds of formula IH are conjugated to a protein as is shown in Scheme 2, by an intermolecular mechanism, the resulting compound is IIH,

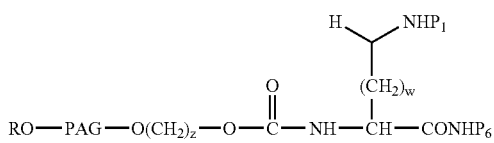

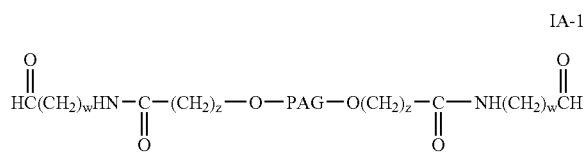
IA-1 wherein PAG, z and w are as above.

The compound of formula IA-1 can be prepared by the following reaction scheme:

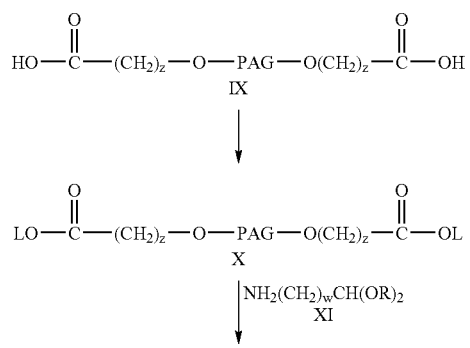

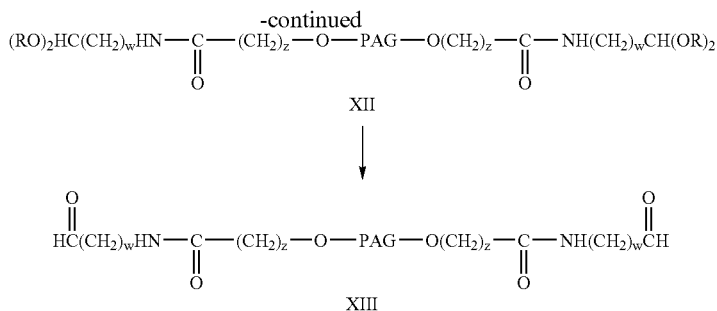

XII

XIII wherein R is lower alkyl, OL is a leaving group, and PAG, z and w are as above.

In the first step of the reaction to produce the compound of formula IA-1, the acid groups of the compound in formula IX are activated to produce the compound of formula X. This is accomplished by activating the acid groups on the compound of formula IX with an activating agent to produce a leaving group such as a N-hydroxy succinimide group. Any conventional method of converting a carboxy group into an activating leaving group such as an N-hydroxy succinimide group can be utilized to produce the compound of formula X. In the next step of the synthesis, the compound of formula X containing the activating leaving group is reacted with the amine acetal compound of formula XI to produce the compound of formula XII. This reaction to form the amide of formula XII is carried out by any conventional means of condensing an amine with an activated carboxylic acid group. The compound of formula XII has the aldehyde protected as its acetal, preferably a lower alkyl acetal. Any conventional aldehyde protecting groups such as other alkyl acetals can also be utilized. The acetal of formula XII can then be hydrolyzed to form the corresponding aldehyde of formula XIII. Any conventional means of hydrolyzing an acetal to form the corresponding aldehyde can be utilized to convert the compound of formula XII into the corresponding aldehyde of formula XIII (IA-1).

In accordance with an other embodiment of preparing a compound of the formula I-A1, the acetal of formula XI is replaced with a dioxolane of the formula XIa that is reacted with compound X to produce the intermediate of XIIa. Compound XIIa is then hydrolyzed to the corresponding vicinal diol and then oxidized with periodate to produce the aldehyde of formula I-A1.

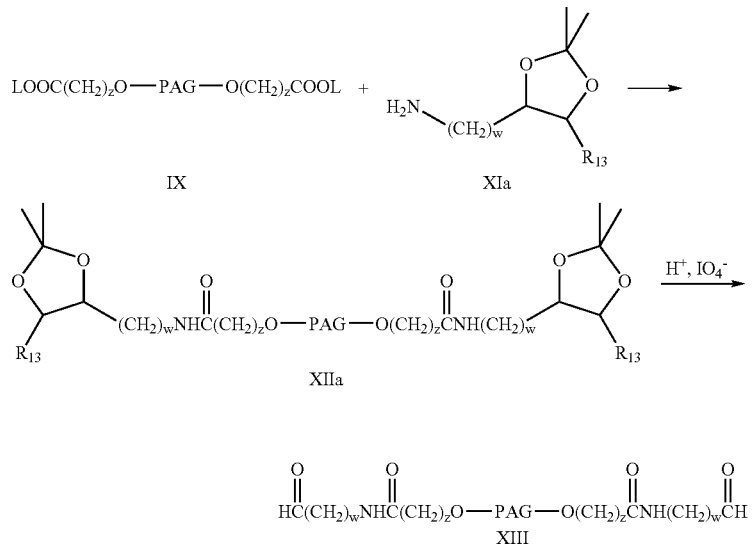

wherein PAG, z and w are as above, OL is a leaving group, and $R_{13}$ is hydrogen, alkyl, or phenyl.

In the compound of formula IA where m is 1, X is —NH— and Y is —O—, this compound has the formula:

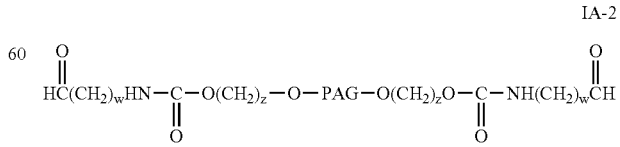

IA-2 wherein PAG, w and z are as above.

The compound of IA-2 can be prepared by the following scheme:

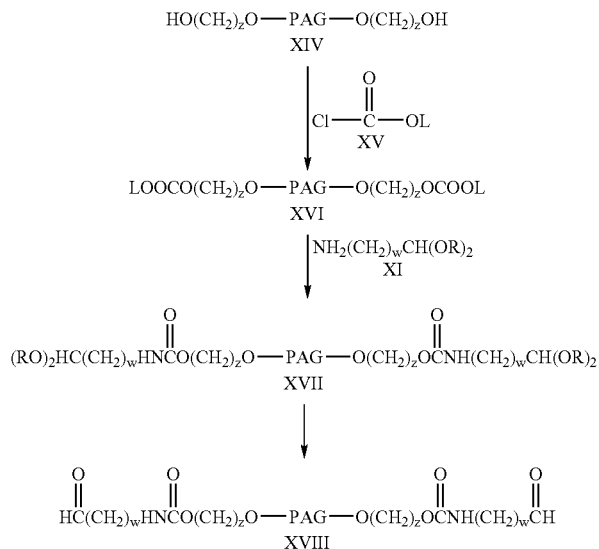

wherein R, OL, PAG, z and w are as above.

In the above reaction scheme the compound of formula XIV is first reacted with a compound of formula XV which is a halo formate containing a leaving group. Any conventional leaving group can be utilized such as the leaving groups herein before mentioned. The preferred leaving group is a para-nitro phenol radical. Any of the conventional conditions for reacting an alcohol such as the compound of formula XIV with a chloro formate such as the compound of formula XV to produce the carbonate of formula XVI may be employed. The carbonate is then reacted with the amine of formula XI to produce the compound of formula XVII. This reaction is carried out as described hereinbefore with regard to reacting the compound of formula X with the compound of formula XI. The compound of formula XVII is then hydrolyzed to produce the compound of formula XVIII (IA-2) in the conventional manner as described in connection with the hydrolysis of the compound of formula XII hereinbefore.

In accordance with an other embodiment of preparing a compound of the formula I-A2, the acetal of formula XI is replaced with a dioxolane of the formula XIa that is reacted with compound XVI to produce the intermediate of XVIIa. Compound XVIIa is then hydrolyzed to the corresponding vicinal diol and then oxidized with periodate to produce the aldehyde of formula I-A2 (XVIII).

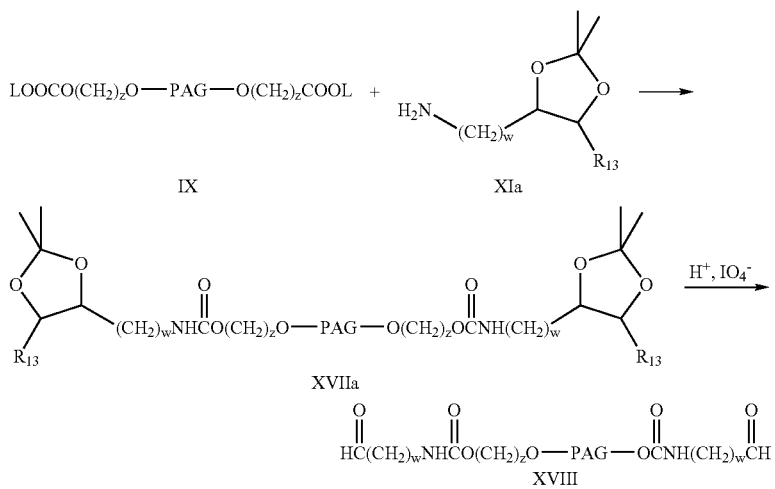

wherein PAG, z and w are as above, OL is a leaving group, and $R_{13}$ is hydrogen, alkyl, or phenyl.

In accordance with another embodiment of this invention wherein the compound of formula IA, m is 1 and Y and X are both —NH—, this compound has the formula:

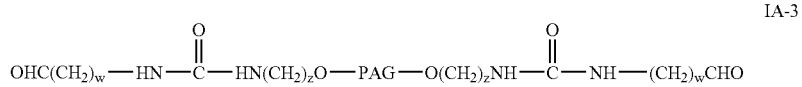

IA-3 wherein PAG, z and w are as above.

The compound of IA-3 can be prepared by the following scheme:

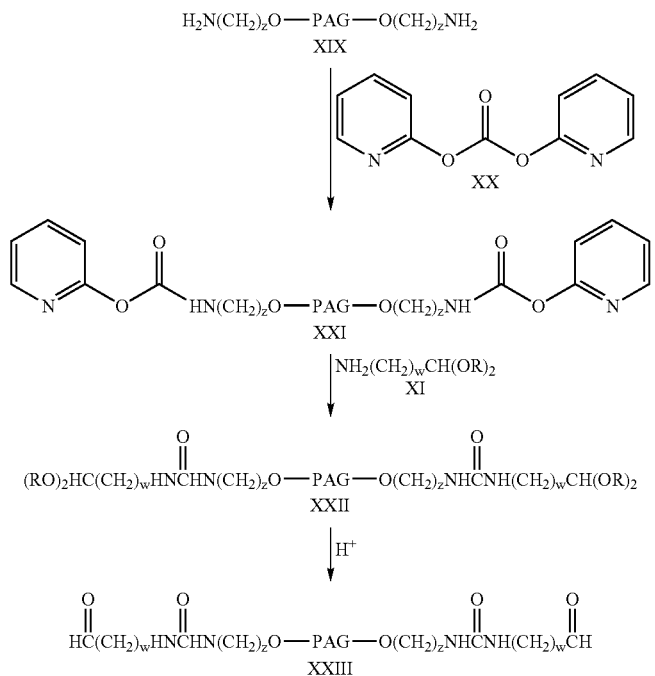

wherein PAG, R is lower alkyl, z and w are as above.

In accordance with this embodiment, the compound of formula XIX is condensed with the compound of formula XX in a halogenated hydrocarbon solvent to produce the compound of formula XXI. This reaction utilizes conventional condensing procedures commonly used in reactions between an activated carbonate and an amine. The compound of formula XXI is condensed with the amine of formula XI in an inert organic solvent to produce the acetal of formula XXII. Any conventional inert organic solvent can be used in this reaction. The acetal of formula XXII is then hydrolyzed in acidic medium, in the manner described hereinabove to produce the compound of formula XXIII (IA-3).

In the same manner as described in the alternate synthesis of IA-2, the compound of formula XIa is reacted with the carbamate XXI to produce the compound of formula XXIIa which is then hydrolyzed and oxidized to give the aldehyde IA-3.

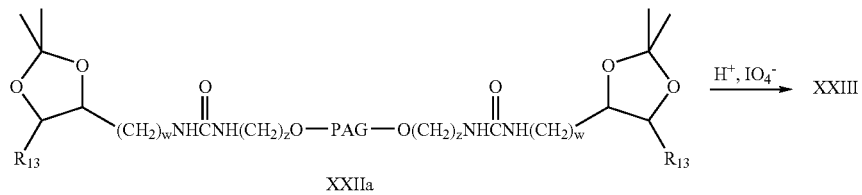

wherein PAG, $R_{13}$, z and w are as above.

In the compound of formula IA where m is 1, Y is —NH— and X is —O— the compound has the following formula:

IA-4 wherein PAG, z and w are as above.

The compound of formula IA-4 can be prepared as shown by the following reaction scheme.

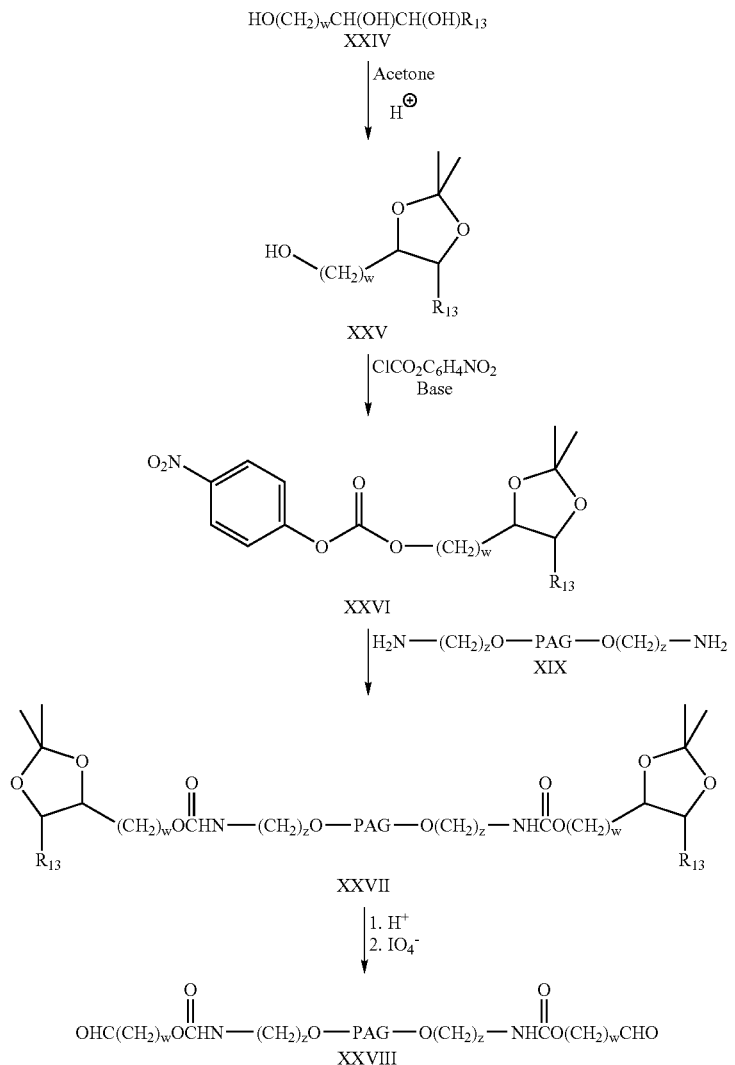

wherein PAG, $R_{13}$, z and w are as above.

In this reaction, the starting material of formula XXIV is a tri-hydroxy compound having a terminal primary hydroxy group which is separated by at least two carbon atoms from two other hydroxy groups that are vicinal to each other. The compound of formula XXIV is converted to its acetonide derivative of formula XXV by reacting the two vicinal hydroxy groups with acetone leaving free the third hydroxy group. Any conventional method of forming an acetonide derivative from the two vicinal hydroxy groups can be utilized to carry out this reaction to form the compound of formula XXV. Reagents other than acetone, such as 2-pentanone, which are known to form cyclic acetals with 1,2-diols, may also be used. The free hydroxy group in the acetonide derivative of formula XXV is then activated with an activating group such as the para-nitro phenyl chloro formate as is shown in the reaction scheme. This reaction to convert the hydroxy group into an activated derivative is well known in the art. In this manner the compound of formula XXVI is produced where the primary hydroxy group on the compound of formula XXV is activated. The compound of formula XXVI is then condensed with the PEG diamine of formula XIX to form the condensation product of formula XXVII. Any conditions conventional in reacting an activated alcohol with an amine to produce a urethane can be utilized to carry out this condensation. The compound of formula XXVII containing the acetonide is then cleaved utilizing conditions conventional in cleaving acetonides such as by treatment with a mild acid, to produce the corresponding dihydroxy compound. The vicinal dihydroxy groups are then oxidized with mild oxidizing agents such as a periodate oxidizing agent to produce the aldehyde of formula XXVIII (IA-4). Any conventional method of oxidizing a vicinal di-hydroxy compound to the corresponding aldehyde can be utilized to carry out this conversion.

The compounds of formula IB may be prepared as described by the following

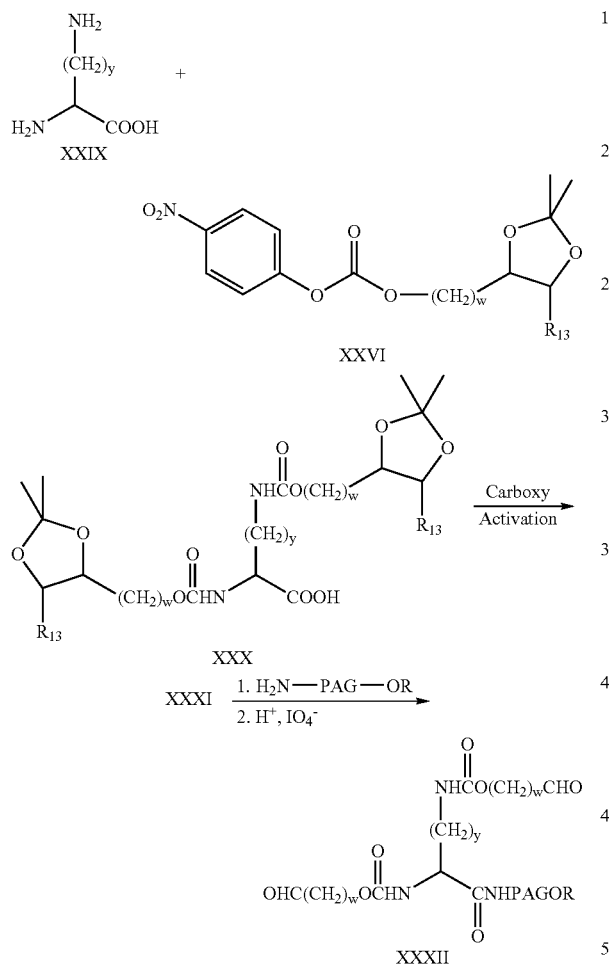

reaction scheme:
wherein R is hydrogen or lower alkyl, and PAG, $R_{13}$, w and y are as above.

The compound of formula XXVI is condensed with the diamine of formula XXIX to form the condensation product of formula XXX. This reaction proceeded in the same manner as previously described for the reaction of compound XIX and XXVI. Any conditions conventional in reacting an activated alcohol with an amine to produce a urethane can be utilized to carry out this condensation. The carboxy group of compound XXX was then activated to give XXXI in the same manner as described for compound IX and the product then condensed with a PAG amine to give the corresponding amide derivative. The acetonides were then cleaved utilizing conditions conventional in cleaving acetonides such as by treatment with a mild acid, to produce the corresponding dihydroxy compound. The resulting dihydroxy groups are then oxidized with mild oxidizing agents such as a periodate oxidizing agent to produce the aldehyde of formula XXXII (IB). Any conventional method of oxidizing a vicinal di-hydroxy compound to the corresponding aldehyde can be utilized to carry out this conversion.

The compound of formula IC is synthesized as described by the following reaction scheme:

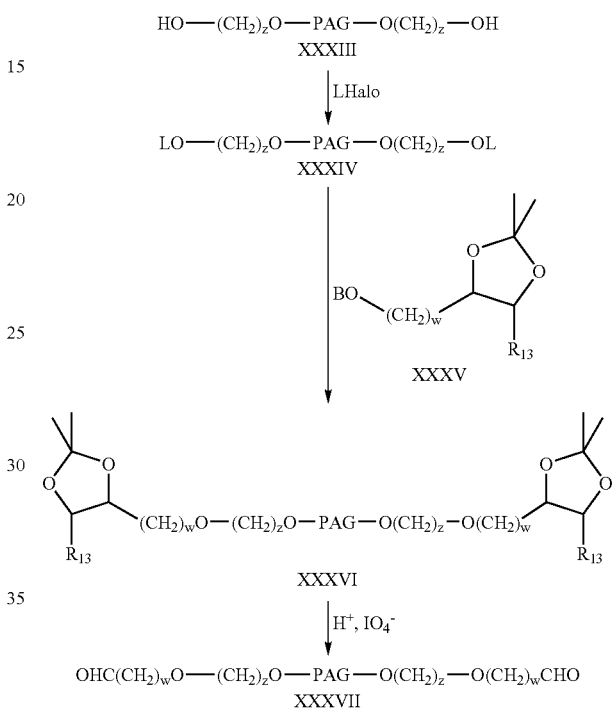

wherein PAG, $R_{13}$, w and z are as above, L is a sulfonyl group, B is an alkalai metal salt, and Halo is a halogen.

In carrying out this process, the compound of formula XXXIII is converted to the compound of formula XXXIV by reacting the hydroxy groups of compound formula XXXIII with an activating leaving group. The conversion of the terminal hydroxyl group of compound XXXIII into an activated leaving group, can be readily achieved by reaction with any conventional method for converting the hydroxy group of compound XXXIII with an activating leaving group such as a tosylate or mesylate. This reaction may be carried out by condensing the compound of formula XXXIII with a halide of an activating leaving group such as tosyl chloride. The compound of formula XXXIV can then be condensed with the alkoxide of formula XXXV to form the compound of formula XXXVI. In this case the acetonide group is a precursor to the aldehyde of formula IC. In the case shown in the above reaction scheme where an acetonide is used, the acetonide can be hydrolyzed in mild acid. However any conventional means to produce the resulting dihydroxy compound from an acetonide can be used in this conversion. The dihydroxy compound resulting form this hydrolysis can then be oxidized with a periodate to give the aldehyde XXXVII (IC).

In accordance with this invention, in formula ID, when m is 0 and X is —NH—, these compounds have the formula:

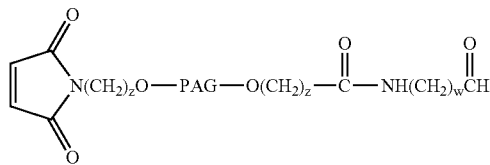

wherein PAG, z and w are as above.

The compound of formula ID-1 is synthesized as shown by the following reaction scheme:

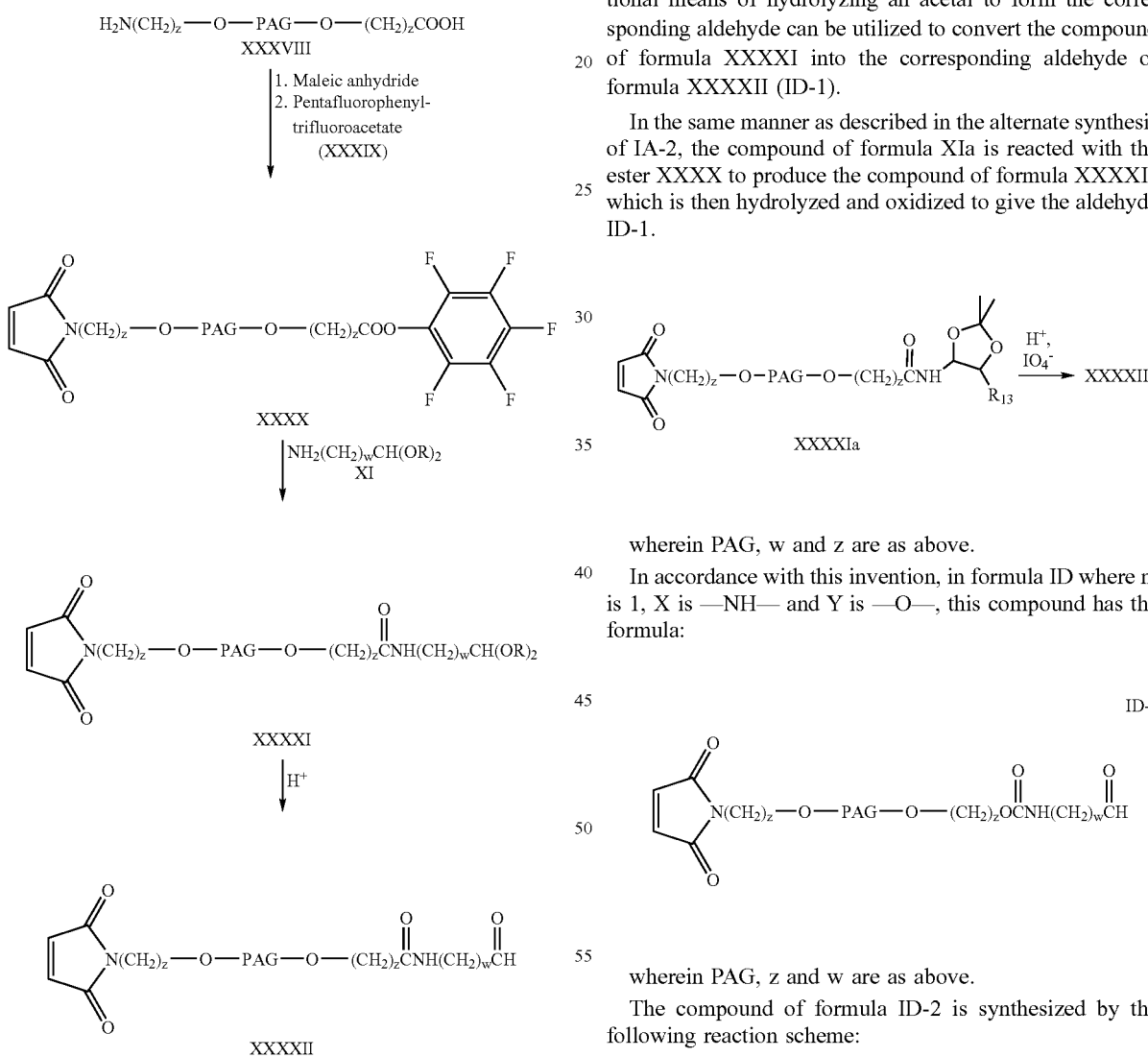

wherein PAG, w and z are as above, and R is lower alkyl.

The compound of type XXXX, may be prepared from the amino acid XXXVIII by modification of a procedure described by Adamczyk et al. Org. Prep. Proced. Int. (1993) 25 592. In carrying out this process, the amino acid XXXVIII is reacted with maleic anhydride and pentafluorophenyl triflouroacetate (XXXIX) in a one-pot procedure to give directly the •-N-maleimidyl-T-pentafluorophenyl ester-PEG derivative XXXX. In the next step of the synthesis, the pentafluorophenyl ester of compound formula XXXX is reacted with the amine acetal compound of formula XI to produce the compound of formula XXXXI. This reaction to form the amide of formula XXXXI is carried out by any conventional means of condensing an amine with an activated carboxylic acid group. The compound of formula XXXXI has the aldehyde protected as its acetal, preferably a lower alkyl acetal. Any conventional aldehyde protecting groups such as other alkyl acetals can also be utilized. The acetal of formula XXXXI can be hydrolyzed to form the corresponding aldehyde of formula XXXXII. Any conventional means of hydrolyzing an acetal to form the corresponding aldehyde can be utilized to convert the compound of formula XXXXI into the corresponding aldehyde of formula XXXXII (ID-1).

In the same manner as described in the alternate synthesis of IA-2, the compound of formula XIa is reacted with the ester XXXX to produce the compound of formula XXXXIa which is then hydrolyzed and oxidized to give the aldehyde ID-1.

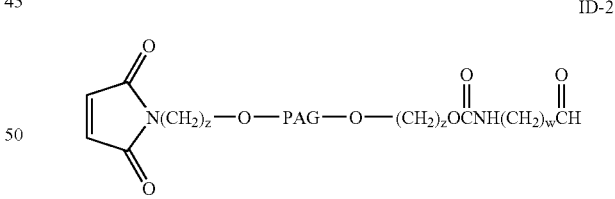

wherein PAG, w and z are as above.

In accordance with this invention, in formula ID where m is 1, X is —NH— and Y is —O—, this compound has the formula:

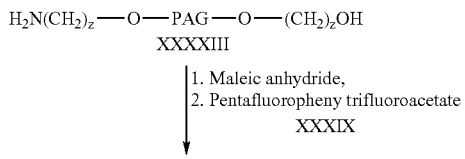

wherein PAG, z and w are as above.

The compound of formula ID-2 is synthesized by the following reaction scheme:

H$_2$N(CH$_2$)$_z$—O—PAG—O—(CH$_2$)$_z$OH
XXXXIII

1. Maleic anhydride,
2. Pentafluoropheny trifluoroacetate
XXXIX

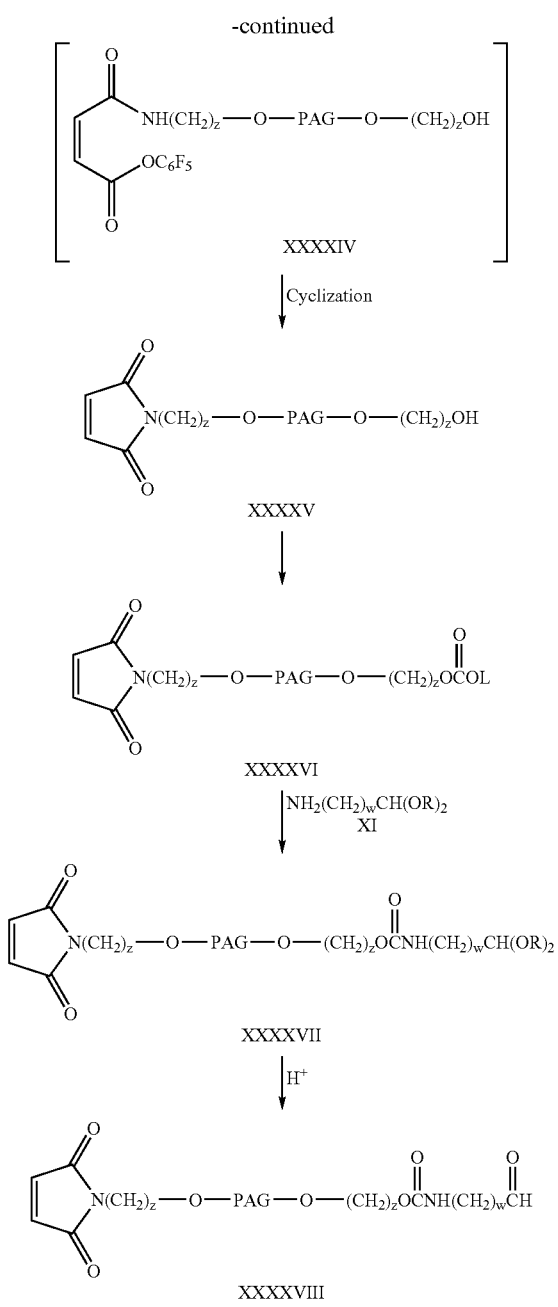

wherein PAG, OL, z and w are as above, and R is lower alkyl.

In the above reaction scheme the compound of formula XXXXIII is reacted with pentafluorophenyl trifluoroacetate (XXXIX) and maleic anhydride to give the maleimide derivative XXXXV via the intermediate XXXXIV. The alcohol function in compound XXXXV is then activated with any conventional leaving group OL such as a phenyl-carbonate derivative or an N-succinimydl carbonate to give compound XXXXVI. The carbonate XXXXVI is then reacted with the amine of formula XI to produce the urethane compound of formula XXXXVII. This reaction is carried out as described hereinbefore with regard to reacting the compound of formula XVI with the compound of formula XI. The compound of formula XXXXVII is then hydrolyzed to produce the compound of formula XXXXVIII (ID-2) in the conventional manner as described in connection with the hydrolysis of the compound of formula XVII hereinbefore.

In the same manner as described in the alternate synthesis of ID-1, the compound of formula XIa is reacted with the ester XXXXVI to produce the compound of formula XXXXVIIa which is then hydrolyzed and oxidized to give the aldehyde ID-2.

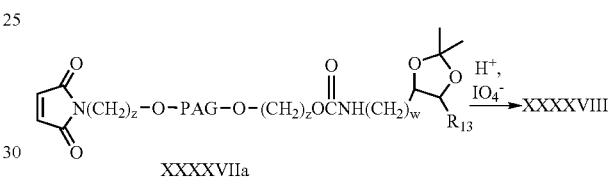

wherein PAG, $R_{13}$, z and w are as above.

In accordance with this invention, in formula IE, when m is 0 and X is —NH—, these compounds have the formula:

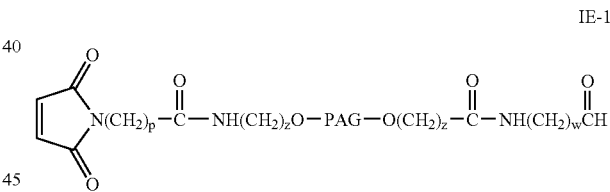

wherein PAG is a divalent residue of polyalkylene glycol resulting from removal of the terminal hydroxy groups and having a molecular weight of from 500 to 100,000 Daltons, z is an integer of from 2 to 4, p is an integer of from 1 to 10, and w is an integer of from 2 to 8.

The compound of formula IE-1 is synthesized by the following reaction scheme:

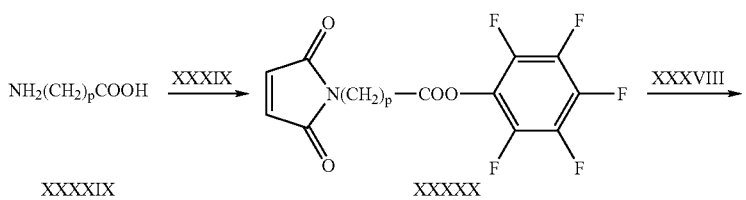

-continued

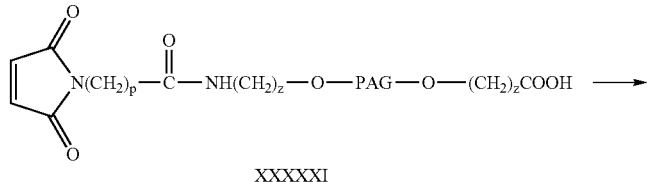

XXXXXI

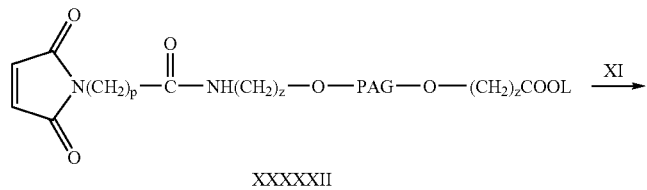

XXXXXII

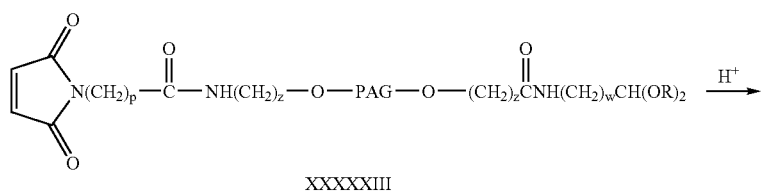

XXXXXIII

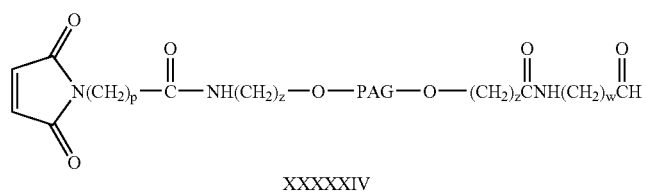

XXXXXIV wherein PAG, p, w and z are as above, OL is an activating leaving group, and R is lower alkyl.

In carrying out this process, the compound of formula XXXXIX is reacted with pentafluorophenyl trifluoroacetate (XXXIX) and maleic anhydride in a one-pot procedure to produce the activated ester derivative of formula XXXXX. The reaction to form the amide of formula XXXXXI is carried out by the reaction of the carboxy-amine XXXVIII with the activated carboxylic acid group of compound XXXXX. The carboxyl Group of compound XXXXXI was then activated to give compound XXXXXII. This Conversion was carried out in the same manner as the formation of compound X from IX. In the next step of the synthesis, the compound of formula XXXXXII containing the activating leaving group is reacted with the amine acetal compound of formula XI to produce the compound of formula XXXXXIII. The compound of formula XXXXXIII has the aldehyde protected as its acetal, preferably a lower alkyl acetal. Any conventional aldehyde protecting groups such as other alkyl acetals can also be utilized. The acetal of formula XXXXXIII can be hydrolyzed to form the corresponding aldehyde of formula XXXXXIV. Any conventional means of hydrolyzing an acetal to form the corresponding aldehyde can be utilized to convert the compound of formula XXXXXIII into the corresponding aldehyde of formula XXXXXIV (IE-1).

In the same manner as described in the alternate synthesis of ID-1, the compound of formula XIa is reacted with the ester XXXXXII to produce the compound of formula XXXXXIIIa which is then hydrolyzed and oxidized to give the aldehyde IE-1.

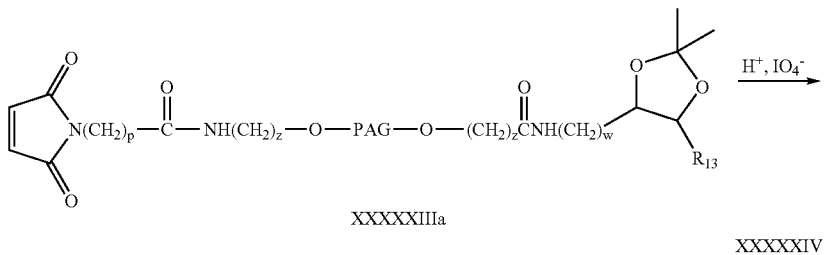

XXXXXIIIa

XXXXXIV wherein PAG, $R_{13}$, p, w and z are as above.

In accordance with this invention, in formula IE where m is 1, X is —NH— and Y is —O—, this compound has the formula:

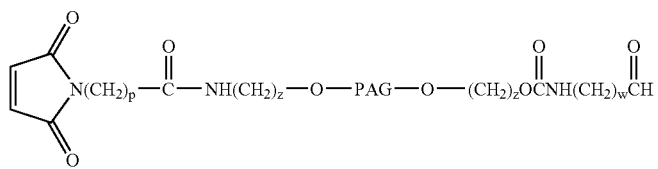

IE-2 wherein PAG, p, w and z are as above.

The compound of formula IE-2 is synthesized by the following reaction scheme:

XXXXX + XXXXIII →

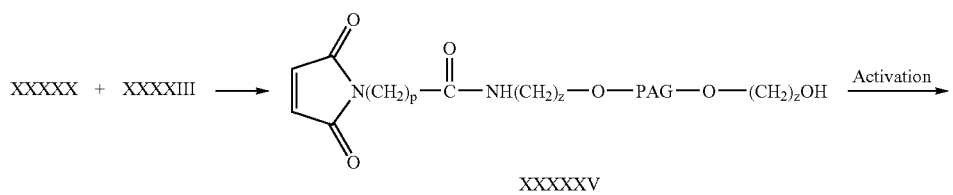

XXXXXV

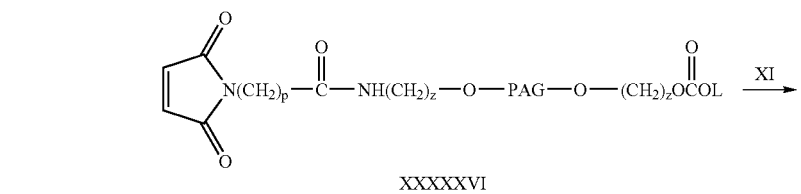

XXXXXVI

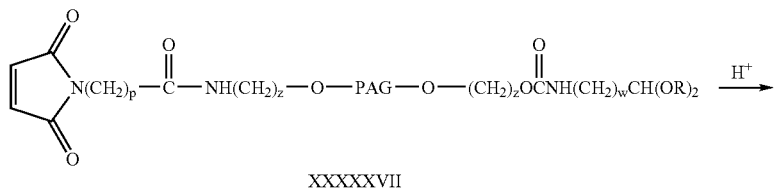

XXXXXVII

XXXXXVIII wherein PAG, p, w and z are as above, OL is an activating leaving group, and R is lower alkyl.

The compound of type XXXXX was prepared as described previously from the amino acid XXXXIX by modification of a procedure described by Adamczyk et al. Org. Prep. Proced. Int. (1993) 25, 592. In the next step of the synthesis, the compound of formula XXXXX is reacted with the amine of formula XXXXIII to produce the amide XXXXXV. The alcohol function in compound XXXXXV is then activated with any conventional leaving group OL such as a phenylcarbonate derivative or an N-succinimydl carbonate to give compound XXXXXVI. The carbonate XXXXXVI is then reacted with the amine of formula XI to produce the urethane compound of formula XXXXXVII. This reaction is carried out as described hereinbefore with regard to reacting the compound of formula XVI with the compound of formula XI. The compound of formula XXXXXVII is then hydrolyzed to produce the compound of formula XXXXXVIII (IE-2) in the conventional manner as described in connection with the hydrolysis of the compound of formula XVII hereinbefore.

In the same manner as described in the alternate synthesis of IE-1, the compound of formula XIa is reacted with the ester XXXXXVI to produce the compound of formula XXXXX-VIIa which is then hydrolyzed and oxidized to give the aldehyde XXXXXVIII.

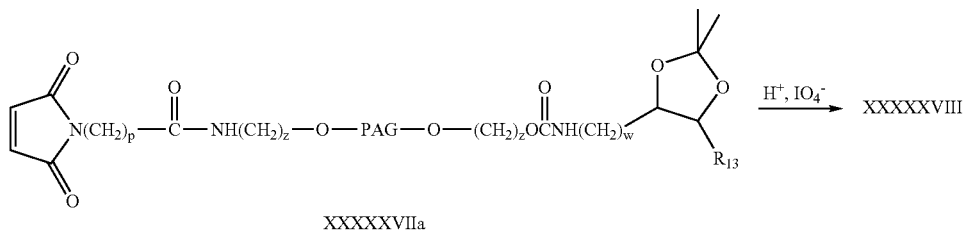

XXXXXVIIa wherein PAG, $R_{13}$, p, w and z are as above.

The compound of formula IF is synthesized from a sulfone of the type XXXXXIX (Shearwater Polymers) by the following reaction scheme:

to reacting the compound of formula XVI with the compound of formula XI. The compound of formula XXXXXX is then hydrolyzed to produce the compound of formula XXXXXXI (IF) in the conventional manner as described in

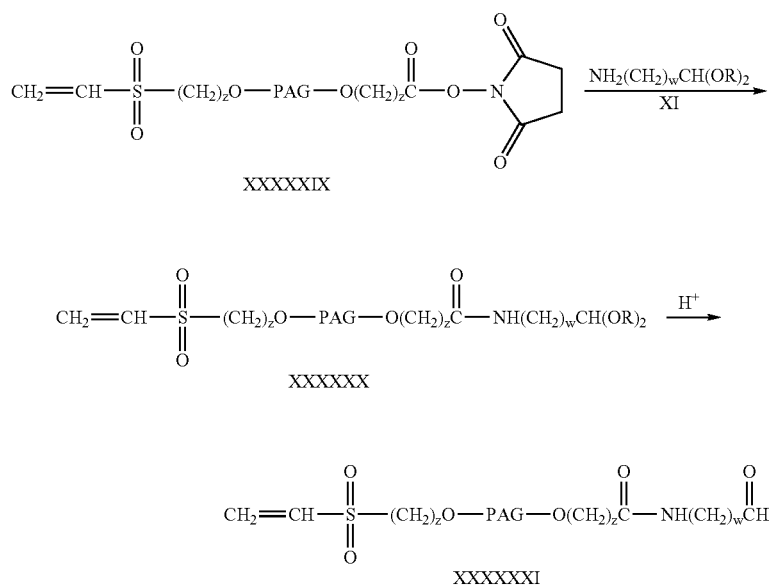

wherein PAG and w are as above, and R is lower alkyl.

In carrying out this process, the N-hydroxy succinimydl ester XXXXXIX is reacted with the amine of formula XI to produce the amide derivative of formula XXXXXX. This reaction is carried out as described hereinbefore with regard connection with the hydrolysis of the compound of formula XVII hereinbefore.

In the same manner as described in the alternate synthesis of IE-1, the compound of formula XIa is reacted with the ester XXXXXIX to produce the compound of formula XXXXXXa which is then hydrolyzed and oxidized to give the aldehyde XXXXXXI.

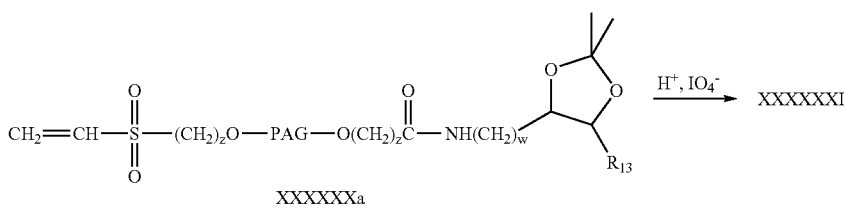

XXXXXXa wherein PAG, $R_{13}$, w and z are as above.

The compound of formula IG is prepared by the following reaction scheme.

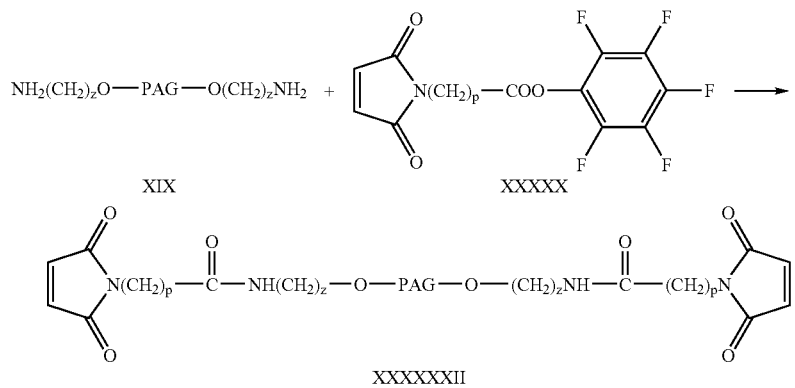

wherein PAG, p and z are as above.

In carrying out this process the PAG reagent XIX is reacted with two moles of the maleimido ester XXXXX to give the product XXXXXXII (IG).

The compound of formula IH is prepared as shown by the following reaction scheme.

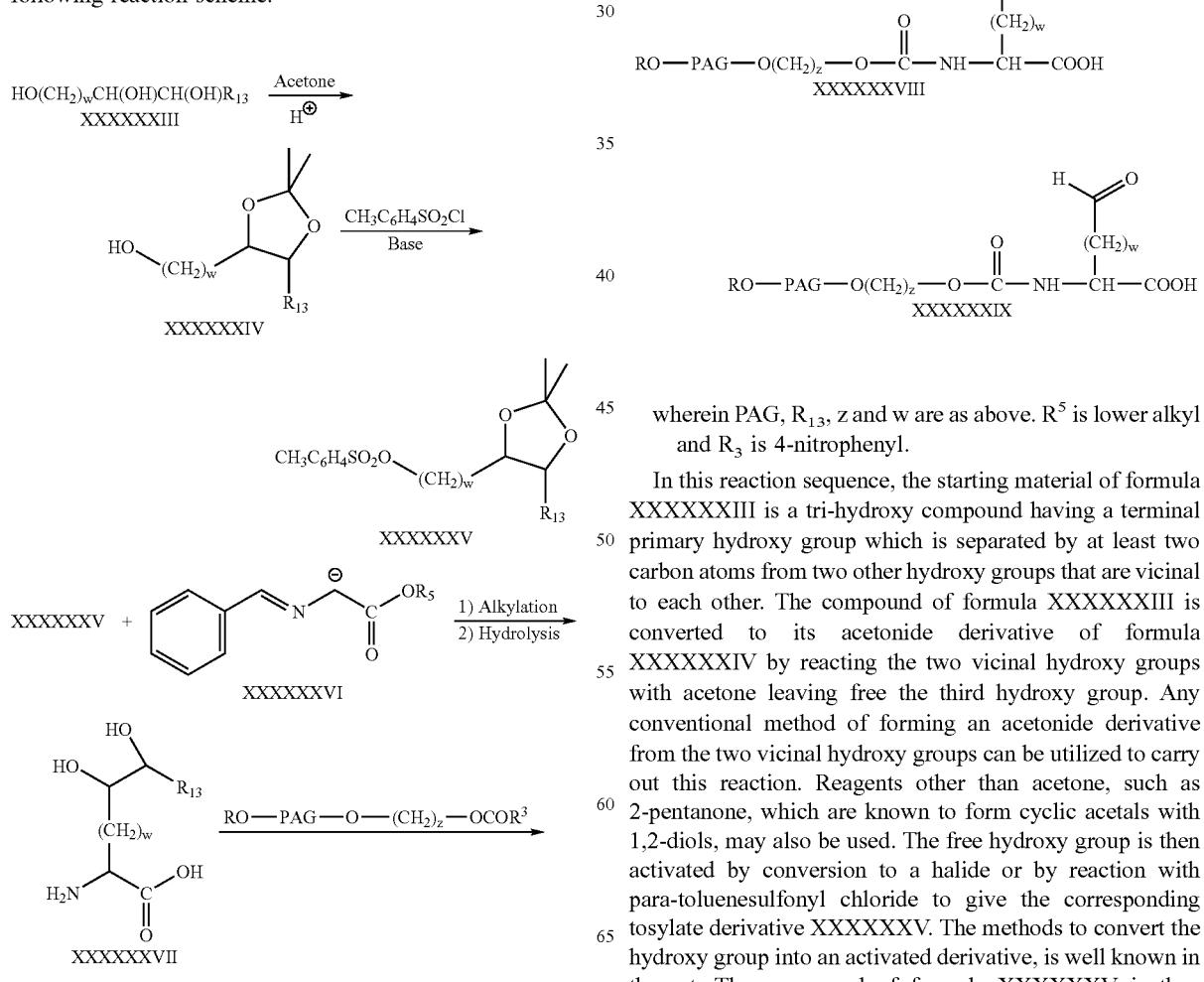

wherein PAG, $R_{13}$, z and w are as above. $R^5$ is lower alkyl and $R_3$ is 4-nitrophenyl.

In this reaction sequence, the starting material of formula XXXXXXIII is a tri-hydroxy compound having a terminal primary hydroxy group which is separated by at least two carbon atoms from two other hydroxy groups that are vicinal to each other. The compound of formula XXXXXXIII is converted to its acetonide derivative of formula XXXXXXIV by reacting the two vicinal hydroxy groups with acetone leaving free the third hydroxy group. Any conventional method of forming an acetonide derivative from the two vicinal hydroxy groups can be utilized to carry out this reaction. Reagents other than acetone, such as 2-pentanone, which are known to form cyclic acetals with 1,2-diols, may also be used. The free hydroxy group is then activated by conversion to a halide or by reaction with para-toluenesulfonyl chloride to give the corresponding tosylate derivative XXXXXXV. The methods to convert the hydroxy group into an activated derivative, is well known in the art. The compound of formula XXXXXXV is then condensed with the •-anion derived from the glycine Schiff base XXXXXXVI to give after hydrolysis the amino acid XXXXXXVII [for the alkylation of glycine derivatives see: a) O'Donnell et al., Tetrahedron Lett., 2641 (1978); b) Stork et al., J. Org. Chem. 41, 3491 (1976); c) Bey et al., Tetrahedron Lett., 1455 (1977)]. The amino group of compound XXXXXXVII may then be reacted selectively with a PAG para-nitrophenyl carbonate derivative to give the carbamate XXXXXXVIII. The vicinal dihydroxy groups are then oxidized with a periodate oxidizing agent to produce the aldehyde of formula XXXXXXIX (IH). Any conventional method of oxidizing a vicinal di-hydroxy compound to the corresponding aldehyde can be utilized to carry out this conversion.

In accordance with an other embodiment of preparing a compound of the formula XXXXXXIX, the acetonide of formula XXXXXXV is replaced with an oxazolidinone of the formula XXXXXXX [see Monneret et al., Tetrahedron Lett. 31, 4879 (1990)] and reacted with compound XXXXXXVI to produce the intermediate XXXXXXXI. Compound XXXXXXXI is then hydrolyzed to the corresponding vicinal amino alcohol XXXXXXXII and then oxidized with periodate to produce the aldehyde of formula XXXXXXXIII. Reaction with a PAG para-nitrophenyl carbonate derivative then affords compound XXXXXXIX.

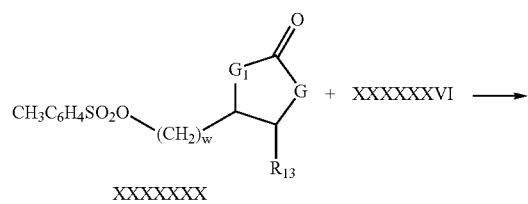

XXXXXXX

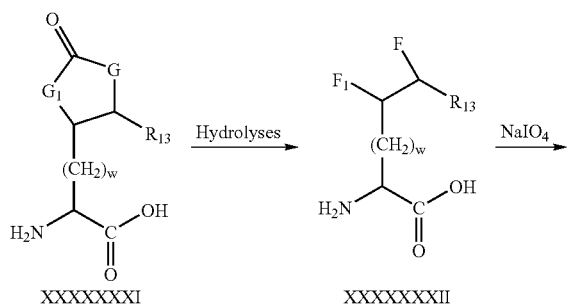

XXXXXXXI                 XXXXXXXII

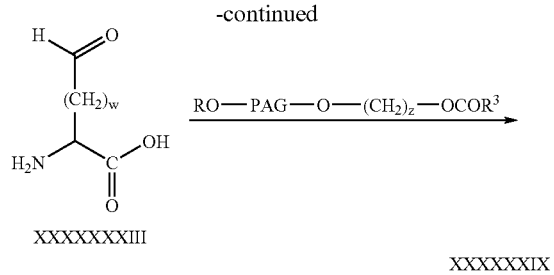

XXXXXXXIII

XXXXXXIX wherein $G_1$ and G are individually selected from —O or —N-Boc with the proviso that $G_1$ is N-Boc when G is —Oo and $G_1$ is —O when G is N-Boc. Wherein $F_1$ and F are individually selected from —OH or —$NH_2$ with the proviso that $F_1$ is —$NH_2$ when F is —OH and $F_1$ is —OH when F is —$NH_2$. $R_3$ is 4-nitrophenyl and $R_{13}$ and w are as above.

The compounds of formula IA, IB, IC, ID, IE IF IG, and IH can be conjugated as described herein before with various proteins through an amino group or free sulfhydryl group which are located on the surface of the protein. The conjugation of a protein to a PEG aldehyde proceeds by the process of reductive amination (see U.S. Pat. No. 5,824,784 dated Oct. 20, 1998) whereas sulfhydryl specific PEG reagents react via a Michael addition and the formation of a thioether bond. By means of regulating the pH from about 5.5 to 7.5, the aldehydes in this invention may condense at the N-terminus amino group of a protein so as to obtain a monoconjugate derivative. In this manner, the pegylating reagents of IA, IB, IC, ID, IE IF, and IH can from site specific mono-conjugates with the N-terminal amino group of various proteins thereby avoiding the necessity of employing extensive purification or separation techniques. On the other hand, if higher pH's from about 8.5 and above are utilized, the reductive amination procedure will also involve the various lysine amino groups which are available in the protein molecule. The hetero-bifunctional reagents of formula ID, IE IF, and IH contain in addition to an aldehyde function, either a sulfhydryl specific group or a carboxyl function. Because of the very large difference inherent in the activities of the two functional groups found in these compounds, the sequence of steps in the cross-linking process may be proceed in a controlled and site-specific manner. In the case of the reagent IG, only sulfhydryl groups may react. Among the preferred proteins for such conjugations are included G-CSF, GM-CSF, hemoglobin, interferon-• interferon-• EPO and the immunoglobulins such as IgG, IgE, IgM, IgA and IgD. When the conjugation is intramolecular, the preferred protein is hemoglobin. In accordance with this invention, when the embodiments of formula IA-1, IA-2, IA-3 IA-4, ID-1, ID-2, IE-1 and IE-2 are reacted with proteins by reactions as shown in Schemes 1 and 2, the following intermolecular and intramolecular compounds are produced:

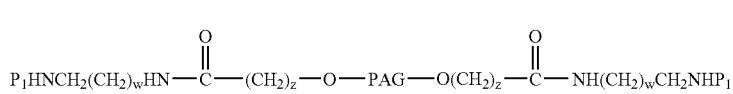

IIA-1

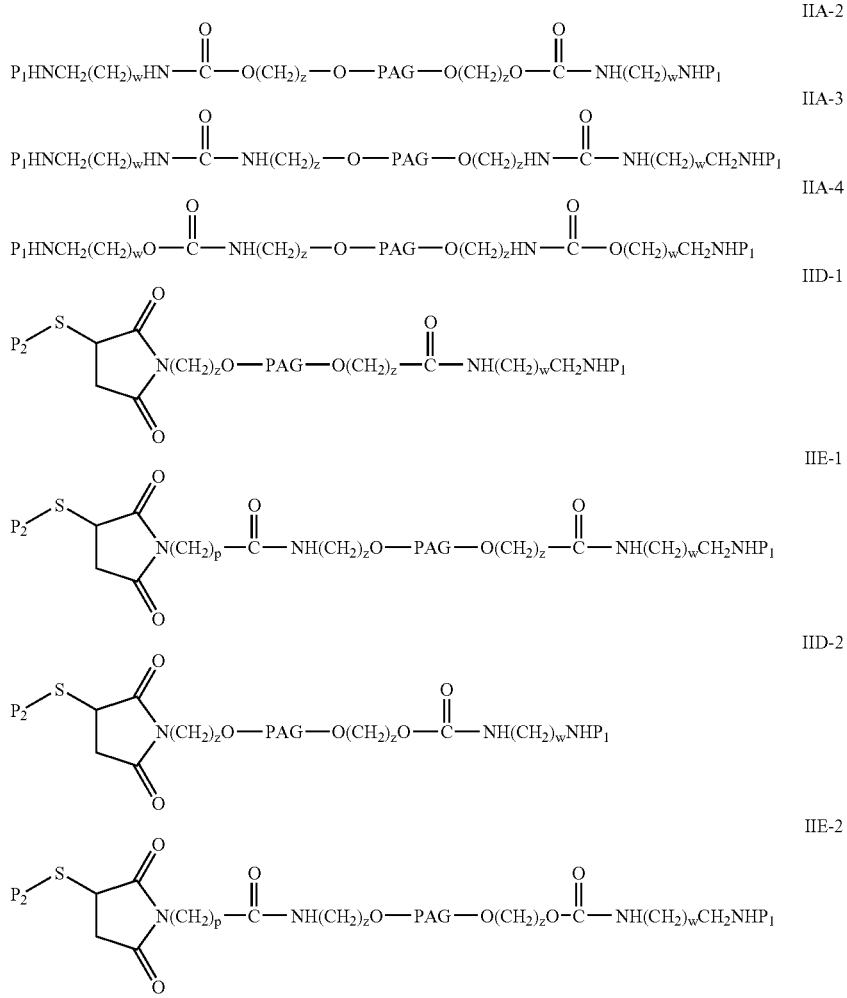
wherein $P_1$, $P_2$, PAG, p, w and z are as above.
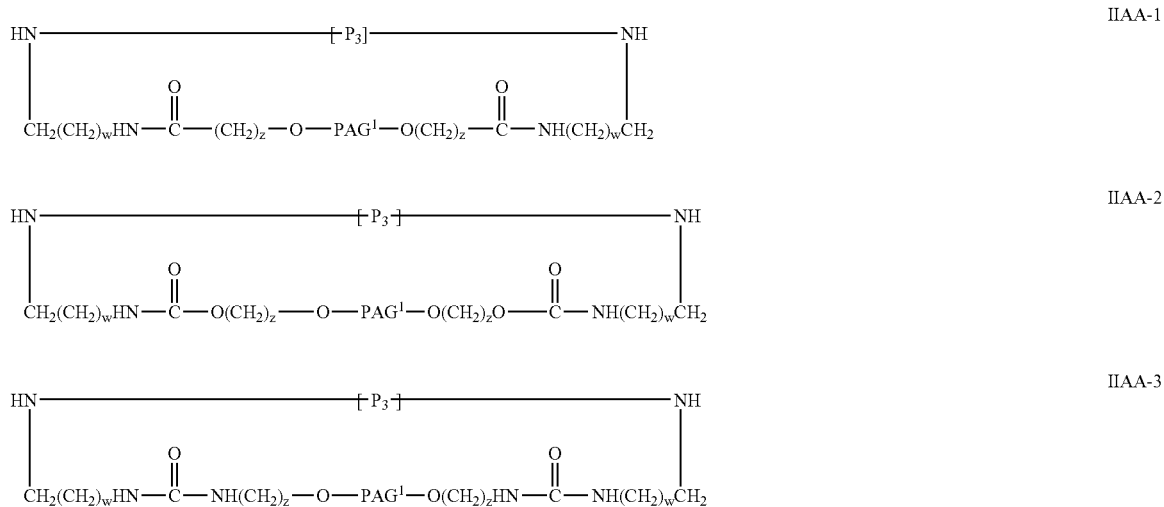

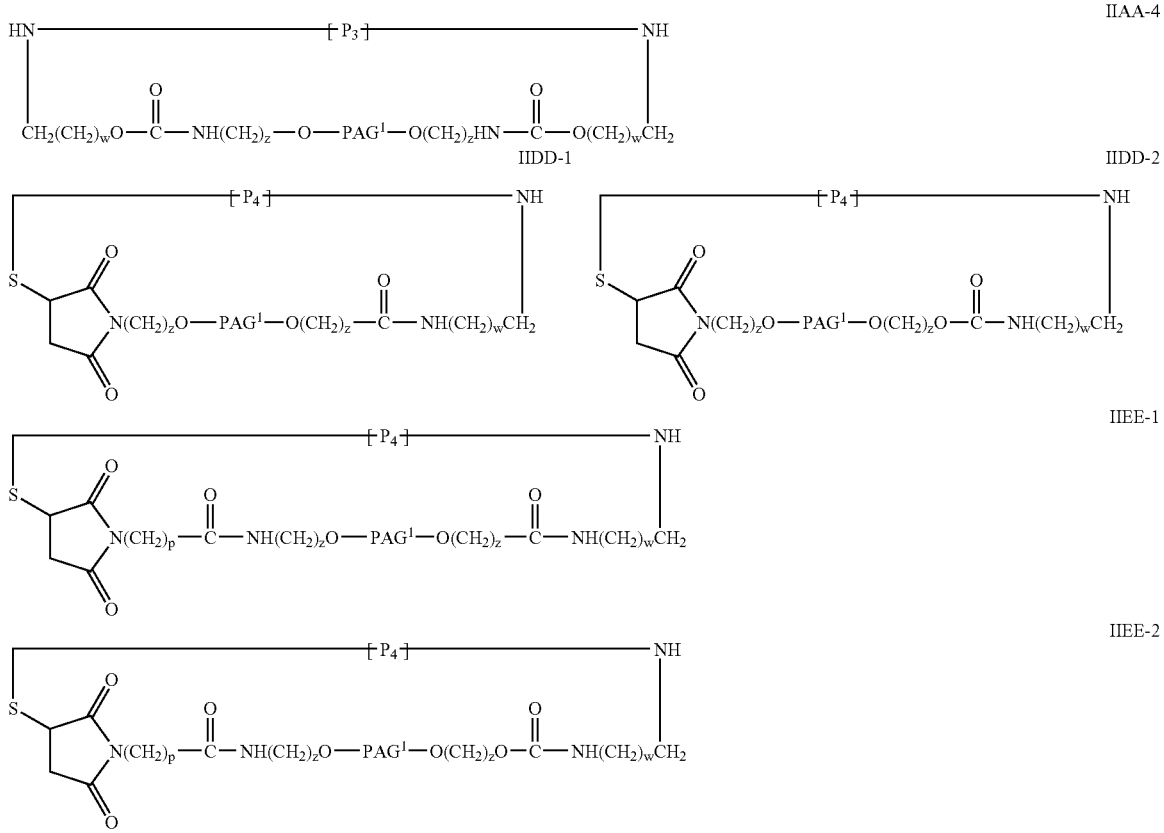

wherein, [P₃], [P₄], PAG¹, p, w and z are as above.

EXAMPLES

The following examples are illustrative of the invention and are not to be construed as limiting the invention. In the following examples, the numbering as "1" etc. refers to the reaction scheme following the descriptive portions in each example.

Example 1

Scheme A (Type IA-1)

Synthesis of PEG-acetamide-propionaldehyde

Polyethylene glycol, HO-PEG-OH (M.W. 20,000, n=453)) 1 and potassium t-butoxide were dissolved in t-butyl alcohol and stirred at 60° C. Ethyl bromoacetate (2.5 moles) was then slowly added and the mixture stirred for 15 hours at 80–85° C. The reaction mixture was then filtered, and the solvent evaporated under reduced pressure. The residue was dissolved in distilled water, washed with diethyl ether, and extracted twice with dichloromethane. The dichloromethane solution was dried over magnesium sulfate and the solvent removed under vacuum. Precipitation was induced by the addition of diethyl ether to the crude residue and the precipitated compound was then filtered and dried under vacuum to give the product 2 as a white powder.

The PEG-diethyl acetate 2 was dissolved in 1 N-sodium hydroxide and stirred for 15 hours at room temperature. The reaction mixture was then adjusted to pH 2 with 1 N aqueous solution HCl and extracted twice with dichloromethane. The extracted organic layer was dried over magnesium sulfate and the organic solvent removed. Diethyl ether was then added to the residue and the precipitated compound filtered. The product was dried under vacuum and the resulting diacid obtained as a white powder.

To a solution of the PEG-diacetic acid dissolved in dichloromethane and cooled to 0–5° C., was added a solution of N-hydroxysuccinimide in dichloromethane followed by a solution of dicyclohexylcarbodiimide (DCC) in the same solvent. The reaction mixture was stirred for 15 hours at room temperature. The by-product, dicyclohexylurea, was removed from the reaction mixture by filtration and the residual organic solvent evaporated. The crude residue was then recrystallized from ethyl acetate, filtered, washed twice with diethyl ether and dried for 12 hours under vacuum to afford the PEG-succinimidyl ester 3 as a white powder To a stirred solution of the PEG-succinimidyl ester 3 dissolved in dichloromethane was added at room temperature a solution of 1-amino-3,3-diethoxypropane (4) in the same solvent. The resulting solution was then stirred for 2 hours at room temperature. Precipitation was induced by the addition of diethyl ether. The product was then filtered and recrystalized from ethyl acetate. The recrystalized compound was dried under vacuum to give 5 as a white powder.

The diethyl acetal 5 was dissolved in an aqueous solution containing phosphoric acid (pH1) and stirred for 2 hours at 40–50° C. After cooling the reaction mixture to room temperature, the acidity was reduced to a pH6 by the addition of a 5% aqueous sodium bicarbonate solution. Brine was added and the resulting mixture extracted twice with dichloromethane. The organic layer was dried over magnesium sulfate, filtered and the solvent evaporated under reduced pressure. Precipitation was induced by the addition of diethyl ether to the crude residue. The product was collected and dried under vacuum to give 6 as a white powder.

mmol). The flask was cooled in an ice-water bath and DCC (0.44 g, 2.16 mmol) added. The reaction mixture was stirred at 0° C. for 1 h and at room temperature for 24 h. The precipitated 1,3-dicyclohexylurea (DCU) was removed by filtration, and the filtrate added to ether (50 ml). After cooling to 4° C. the crude material 2 was collected by filtration and purified by precipitating twice from methylene chloride by the addition of ether.

To the N-hydroxy succinate derivative 2 (8.5 g~0.85 mmol) dissolved in dry methylene chloride (25 ml) there

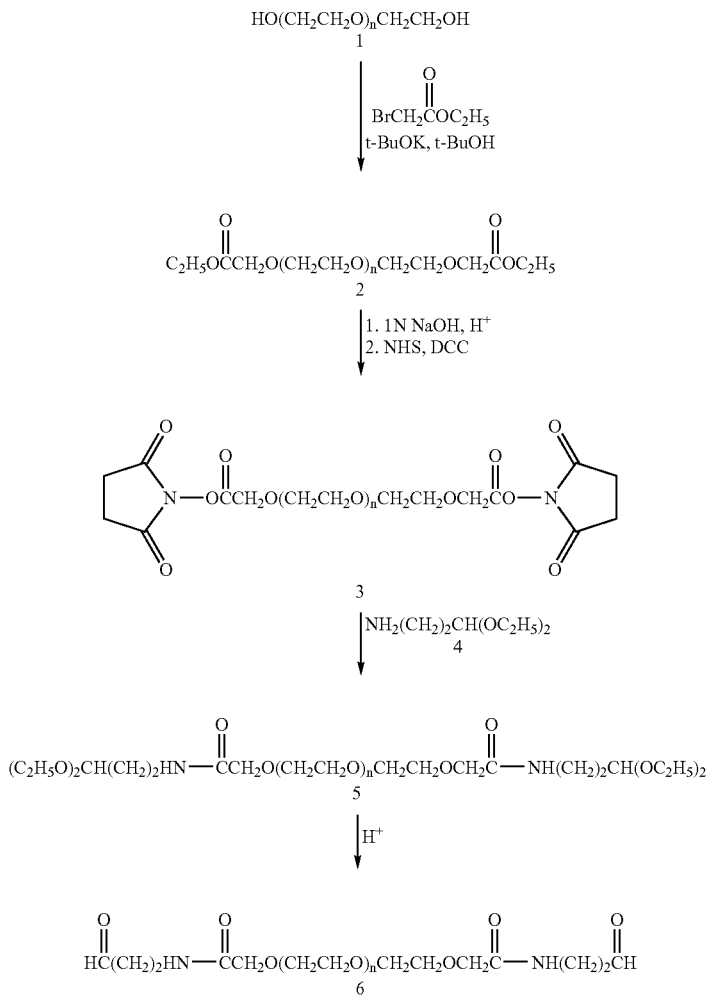

Scheme A

The integer n may be from about 11 to 2,300 but more preferably 11 to 1,000.

Example 2

Scheme B (Type IA-1)

Synthesis of PEG-propionamide-butyraldehyde

To 10 g, (1 mmol) of polyethylene glycol dipropionic acid 1 (MW 10,000, n=224) dissolved in dry methylene chloride (30 ml) was added dry and finely powdered NHS (0.56 g, 5 was added 1-amino-4,4-dimethoxybutane (3) (0.4 g, 2.5 mmol). The reaction mixture was stirred at room temperature for 2 h and the product precipitated in ether (100 ml). After cooling to 4° C. the crude acetal of formula 4 was collected by filtration and precipitated twice from methylene chloride by addition of ether to obtain 8 g of the acetal as a white solid. The acetal was then dissolved in 50 ml of 0.1M HCL and stirred at room temperature for 4 h to produce the amide aldehyde 5. The water was then removed under reduced pressure, and the crude amide-aldehyde product 5 purified by chromatography.

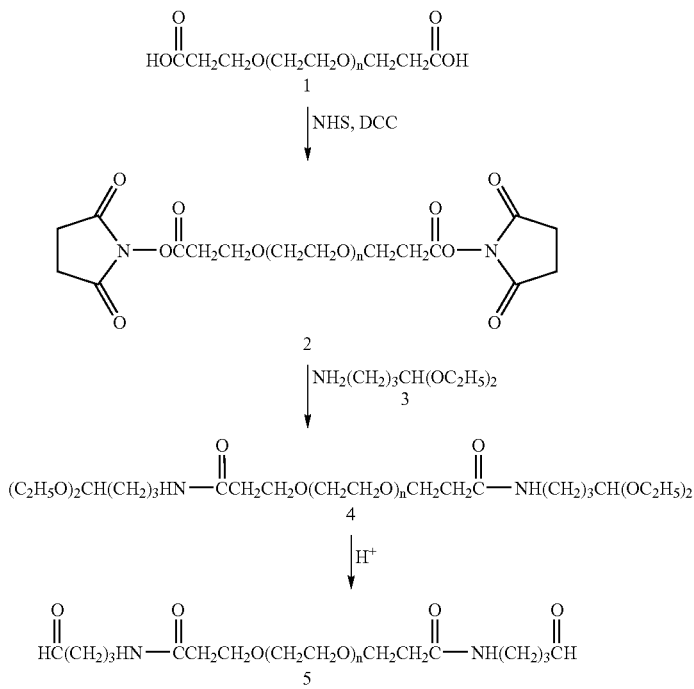

The integer n may be from about 11 to 2,300 but more preferably 11 to 1,000.

Example 3

Scheme C (Type IA-2)

Synthesis of PEG-urethane-propionaldehyde

Triphosgene in dichloromethane was added slowly to a solution of PEG (MW 20,000, n=453) 1 dissolved in dichloromethane and the resulting mixture stirred for 15 hours at room temperature. The organic solvent and excess phosgene were then removed from the reaction mixture under vacuum. The residue was redisolved in dichloromethane and treated with N-hydroxysuccinimide followed by trimethylamine. After 3 hours, the solution was filtered and evaporated to dryness. The residue was dissolved in warm (50° C.) ethyl acetate, and then the solution cooled to 0° C. The resulting precipitate 2 was collected as a white powder, and the product dried under vacuum.

To a solution of the PEG-succinimidylcarbonate 2 dissolved in dichloromethane was added 1-amino-3,3-diethoxypropane (3). The reaction mixture was then stirred for 2 hours at room temperature. Ether was then added and the resulting precipitate 4 collected and recrystalized from ethyl acetate. The product 4 was washed twice with diethylether after filtration and dried under vacuum.

The diethyl acetal 4 was dissolved in an aqueous solution containing phosphoric acid (pH1) and stirred for 2 hours at 40–50° C. After cooling the reaction mixture to room temperature, the acidity was reduced to a pH6 by the addition of a 5% aqueous sodium bicarbonate solution. Brine was added and the resulting mixture extracted twice with dichloromethane. The organic layer was dried over magnesium sulfate, filtered and the solvent evaporated under reduced pressure. Precipitation was induced by the addition of diethyl ether to the crude residue. The product was collected and dried under vacuum to give 5 as a white powder.

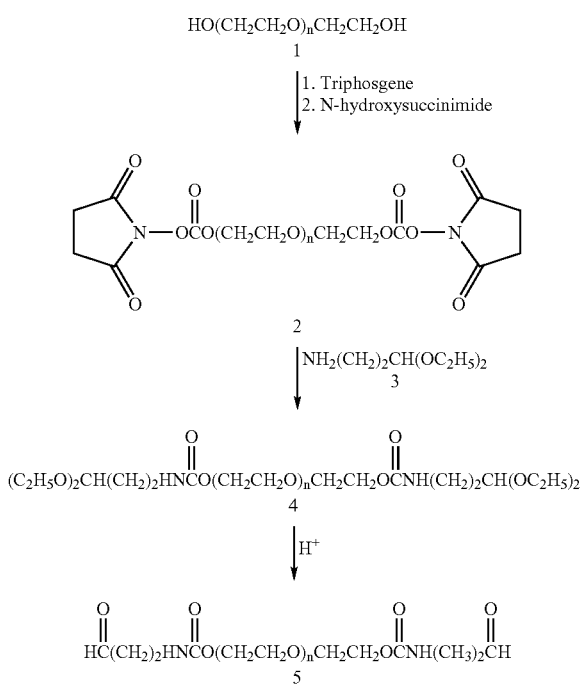

The integer n may be from about 11 to 2,300 but more preferably 11 to 1,000.

Example 4

Scheme D (Type IA-2)

Synthesis of PEG-urethane-butyraldehyde

To a solution of 403.5 mg (2 mmol) of 4-nitrophenyl chloroformate (2) and 237.2 mg (1.94 mmol) of 4-dimethylaminopyridine dissolved in 10 ml of dry methylene chloride was added dropwise a solution of 9.7 g (0.97 mmol) of PEG (10,000 MW, n=226) (1) dissolved in 50 ml of methylene chloride and the solution stirred for 1 h at room temperature. The 4-nitrophenyl carbonate derivative of formula 3 was not isolated but reacted directly with 346 mg (2.35 mmol) of 1-amino-4,4-dimethoxbutane (4). Stirring was continued for 20 h after which time the product 5 was precipitated by the addition of ether (100 ml).

After cooling to 4° C., the crude acetal of formula 5 was collected by filtration and precipitated twice from methylene chloride by addition of ether to give 8 g of the acetal as a white solid. The acetal was then dissolved in 50 ml of 0.1M HCL and stirred at room temperature for 4 h. The water was then removed under reduced pressure, and the crude urethane-aldehyde 6 purified by chromatography.

Scheme D

HO(CH₂CH₂O)ₙCH₂CH₂OH
1

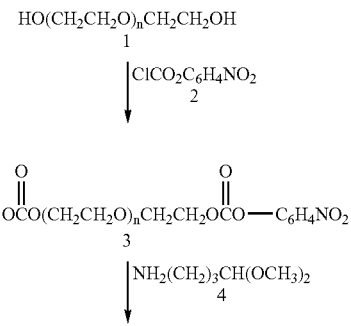

O₂NC₆H₄—OCO(CH₂CH₂O)ₙCH₂CH₂OCO—C₆H₄NO₂
3

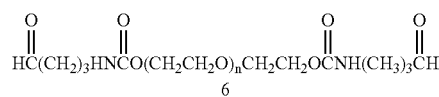

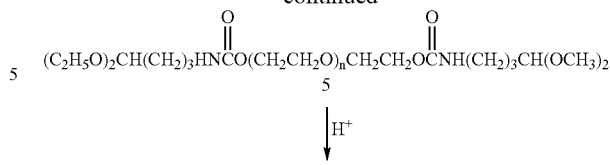

(C₂H₅O)₂CH(CH₂)₃HNCO(CH₂CH₂O)ₙCH₂CH₂OCNH(CH₂)₃CH(OCH₃)₂
5

| H⁺

HC(CH₂)₃HNCO(CH₂CH₂O)ₙCH₂CH₂OCNH(CH₃)₃CH
6

The integer n may be from about 11 to 2,300 but more preferably 11 to 1,000.

Example 5

Scheme E (Type IA-3)

Synthesis of PEG-urea-propionaldehyde

To a solution of 2 g (0.2 mmol) of the diamino PEG of formula 1 (MW 10,000, n=226) in 40 ml of dry methylene chloride, was added at 0° C., 260 mg (1.2 mmol) of di-2-pyridyl carbonate 2 and the mixture stirred for 5 h. The product of formula 3 was then precipitated by the addition of 100 ml of ether, filtered, and washed with an additional 100 ml of ether. The product was then dried under vacuum under a slow stream of nitrogen to give 1.9 g of the compound of formula 3 as a white powder. To the resulting urethane intermediate (1.5 g~1.5 mmol) dissolved in dry methylene chloride (25 ml) was added 1.2 g (~8 mmol) of 1-amino-3,3-diethoxypropane (4). The reaction mixture was stirred at room temperature for 12 h and the acetal of formula 5 precipitated from ether (100 ml). After cooling to 4° C. the crude acetal was collected by filtration and precipitated twice from methylene chloride by addition of ether to obtain 1.1 g of the acetal 5 as a white solid. The acetal was then dissolved in 50 ml of 0.1M HCL and stirred at room temperature for 4 h. The water was then removed under reduced pressure, and the crude urea-aldehyde product of formula 6 purified by chromatography.

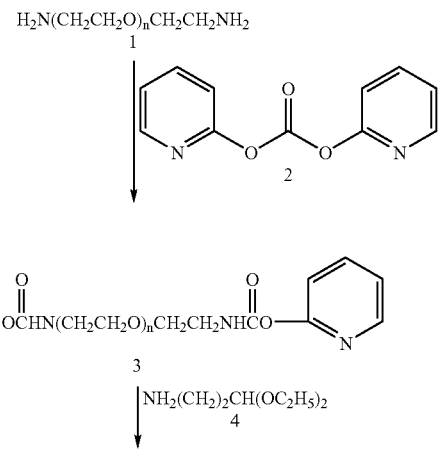

-continued

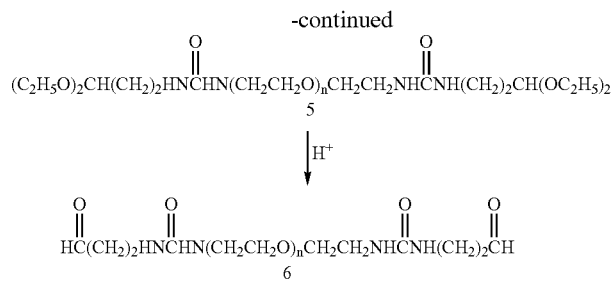

The integer n may be from about 11 to 2,300 but more preferably 11 to 1,000.

Example 6

Scheme F (Type IA-4)

Synthesis of PEG-urethane-butyraldehyde

The pentane-1,2,5-triol of formula 1 (11.7 g, 97.5 mmol) and toluene-p-sulfonic acid (0.3 g) in acetone-light petroleum ether (bp 40–60) (1:1 60 ml) were refluxed 24 h with a Dean-Stark apparatus. The solvent was then removed under vacuum. The residue was then dissolved in ether and the ethereal solution washed with aqueous sodium carbonate, dried ($Na_2CO_3$) and the ether removed. The resulting oil was then distilled to give 10.7 g of the 1,3-dioxolane-2,2-dimethyl-4-propanol of formula 2 bp. 117–118, 12 mm. (Golding et al., (1978) J. C. S. Perkin II, 839).

To a solution of 11.2 g (55 mmol) of 4-nitrophenyl chloroformate in 100 ml of acetonitrile was added slowly 7.3 g (60 mmol) of 4-dimethylaminopyridine followed by 8 g (50 mmol) of the above acetonide product 2 dissolved in 20 ml of acetonitrile. After stirring for 24 h, the precipitated pyridinium hydrochloride was filtered and the solvent removed under reduced pressure. The residue was then dissolved in 200 ml of ether and washed with a 5% aqueous solution of sodium bicarbonate. The ether solution was then dried ($Na_2CO_3$) and the solvent removed under vacuum to give 16 g of the acetonide of formula 3.

To a solution of 6 g (0.6 mmol) of the diamino PEG of formula 4 (MW 10,000, n=226) in 40 ml of dry methylene chloride, was added at 0° C., 392 mg (1.2 mmol) of the 4-nitrophenyl carbonate of formula 3 and 148 mg of 4-dimethylaminopyridine. The solution was stirred for 24 h after which time the compound of formula 5 was precipitated by the addition of 150 ml of ether. This product was filtered and further washed with ether to give 5 g of the urethane-acetonide of formula 5 as a white solid.

The above urethane-acetonide of formula 5 (5 g, 0.5 mmol) was dissolved in 75 ml of 0.1M HCl and stirred for 6 h. The water and HCl were then removed under reduced pressure to give the corresponding diol product. The solution was neutralized to pH7 with 0.1N NaOH and 534 mg of $NaIO_4$ (2.5 mmol) then added. The reaction was then allowed to proceed for 5 h in the dark and the aldehyde of formula 6 isolated by size exclusion chromatography on a Sephadex G 10 column. Oxidation of the 1,2-diol may also be realized using $NaIO_4$ supported on wet silica gel. Using this procedure the aldehyde is obtained without hydrate formation. (see Vo-Quang et al., (1989) Synthesis No. 1, 64).

Scheme F

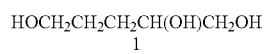

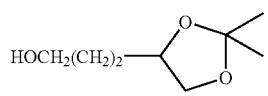

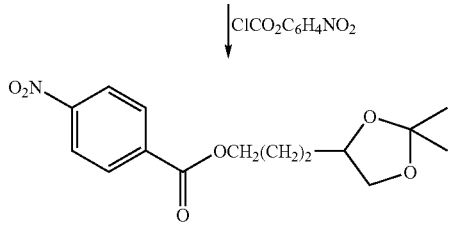

-continued

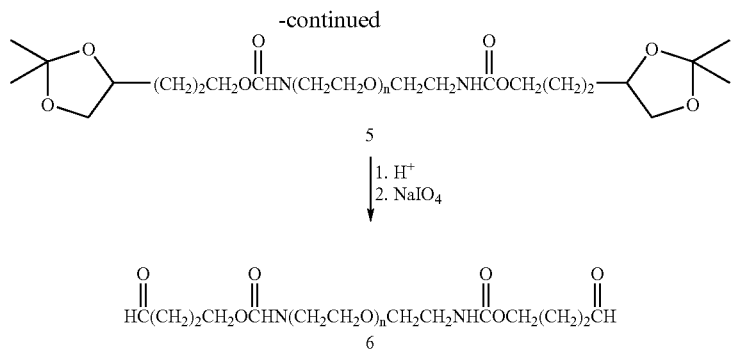

Example 7

Scheme G (Type IB)

Synthesis of Branched PEG-urethane-butyraldehyde

Compound 2 was prepared as described in Example 6 and reacted with lysine (1) in the presence of 4-dimethylaminopyride to give the urethane derivative 3. To a solution of 3 (2.5 g, 5 mmol) dissolved in dichloromethane and cooled to 0–5° C., was added a solution of N-hydroxysuccinimide (2.8 g, 25 mmol) in dichloromethane followed by a solution of dicyclohexylcarbodimide (DCC) (2.2 g, 10.8 mmol) in the same solvent. The reaction mixture was stirred for 15 hours at room temperature. The by-product, dicyclohexylurea, was removed from the reaction mixture by filtration and the residual organic solvent evaporated under vacuum. The crude residue was then recrystalllized from ethyl acetate filtered, washed twice with diethyl ether and dried for 12 hours under vacuum to afford 2.2 g of the N-hydroxy succinimidyl ester.

To a stirred solution of the N-hydroxy succinimidyl ester (0.6 g, 1 mmol) dissolved in dichloromethane was added at room temperature a solution of 10 g mPEG amine (MW 10,000, n=226)) in the same solvent and the resulting solution then stirred for 2 hours at room temperature. Precipitation was induced by the addition of diethyl ether. The product was then filtered and recrystalized from ethyl acetate. The recrystalized compound was dried under vacuum to give 4 as a white powder. The above urethane-acetonide of formula 4 (5.4 g, 0.48 mmol) was dissolved in 75 ml of 0.1M HCl and stirred for 6 h. The water and HCl were then removed under reduced pressure to give the corresponding diol product. To 4 g of the diol dissolved in 75 ml water was added 534 mg of NaIO$_4$ (2.5 mmol) and the reaction allowed to proceed for 5 h in the dark. The aldehyde of formula 5 was then isolated by size exclusion chromatography on a Sephadex G 10 column. Oxidation of the 1,2-diol may also be realized using NaIO$_4$ supported on wet silica gel. Using this procedure the aldehyde is obtained without hydrate formation. (see Vo-Quang et al., (1989) Synthesis No. 1, 64).

Scheme G

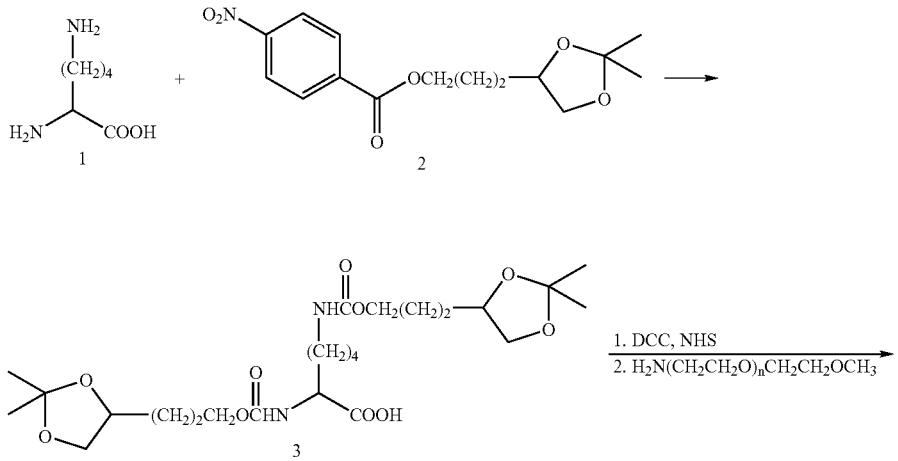

-continued

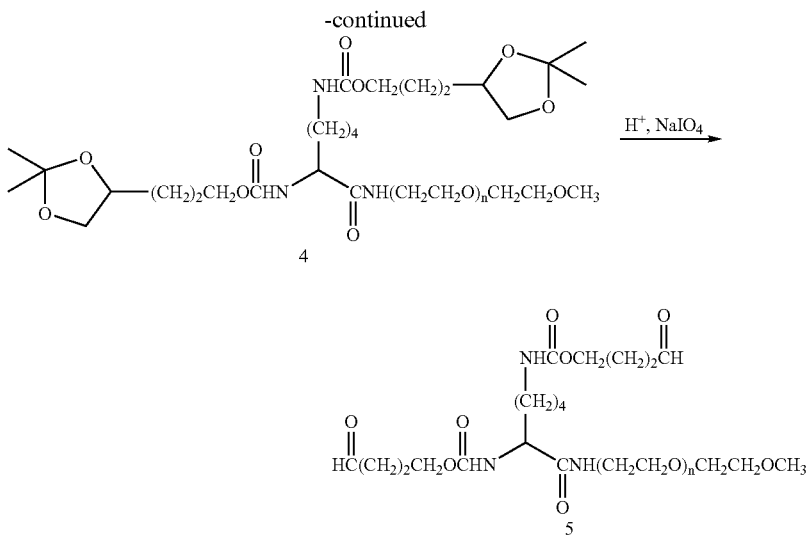

The integer n may be from about 11 to 2,300 but more preferably 11 to 1,000.

Example 8

Scheme H (Type IC)

Synthesis of PEG butyraldehyde

To a solution of 6 g (0.6 mmol) of PEG alcohol (MW 10,000, n=226) of formula 1 in 40 ml of dry methylene chloride, was added at −10° C., 364 mg (0.52 ml) of trimethylamine and toluene-p-sulfonyl chloride (762 mg, 4 mmol). The cooling was removed and the mixture stirred at room temperature for 18 h. The product was precipitated by the addition of 150 ml of ether, filtered and further washed with ether to give 5 g of the compound of formula 2 as a white solid.

A solution of 128 mg (0.8 mmol) of 1,3-dioxolane-2,2-dimethyl-4-propanol (prepared as described in Example 6) dissolved in 10 ml of dry benzene was added dropwise under nitrogen to a mixture of 50 mg of sodium hydride suspended in 5 ml of benzene. The mixture was then stirred for 30 min to give the sodium alkoxide salt of the compound of formula 3. To this solution was then added dropwise over a 20-min period, a solution of 4 g (~0.4 mmol) of the PEG tosylate 2 dissolved in 30 ml of dry dioxane. The reaction mixture was then stirred for 24 h at 40° C. and then added dropwise to 150 ml of ether to precipitate the compound of formula 4 as a white solid. This material was then purified by chromatography on a small alumina column.

The PEG acetonide 4 (3.5 g) was dissolved in 40 ml of 0.1M HCl and stirred for 6 h. The water and HCl were then removed under reduced pressure to give the corresponding diol product. To 3 g of the 1,2-diol dissolved in 40 ml water (~0.3 mmol of diol) was added 160 mg of NaIO$_4$ (0.75 mmol) and the reaction allowed to proceed for 5 h in the dark. Compound 5 was then isolated by size exclusion chromatography on a Sephadex G 10 column. Oxidation of the 1,2-diol may also be realized using NaIO$_4$ supported on wet silica gel. Using this procedure the dialdehyde 5 is obtained without hydrate formation (see Vo-Quang et al., (1989) Synthesis No. 1, 64).

Scheme H

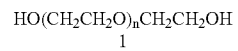
1

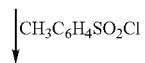

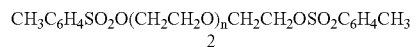
2

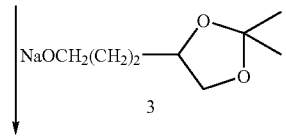

-continued

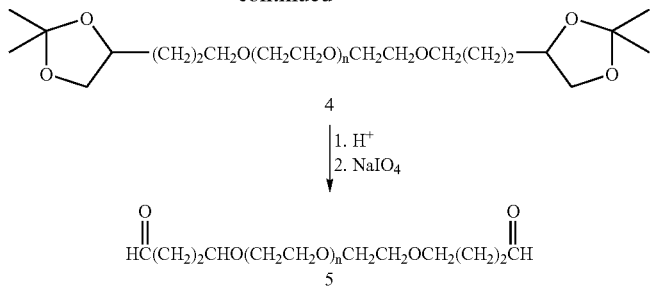

$$\downarrow \begin{array}{l} 1.\ H^+ \\ 2.\ NaIO_4 \end{array}$$

HC(CH₂)₂CHO(CH₂CH₂O)ₙCH₂CH₂OCH₂(CH₂)₂CH

5

The integer n may be from about 11 to 2,300 but more preferably 11 to 1,000.

Example 9

Scheme I (Type ID-1)

Synthesis of PEG maleimido-amide Butyraldehyde

To a solution of maleic anhydride (104 mg, 1.06 mmol), diisopropylethyl amine (0.43 ml, 2.5 mmol) and pentafluorophenyl trifluoroacetate (0.43 ml, 2.5 mmol) dissolved in 30 ml of dry peroxide free dioxane was added 10 g (1 mmol) of •-amino-•-carboxy-PEG 1, (MW 10,000, n=226) dissolved in 40 ml of dry methylene chloride and 5 ml of DMF. The reaction was stirred for eight hours at room temperature, cooled to 0° C. and a 150 ml of dry ether slowly added with stirring. The precipitated maleimide-ester derivative 2 was filtered to give 9 g of product.

To a solution of 10 g (1 mmol) of compound 2 dissolved in dry methylene chloride (25 ml) was added 665 mg (5.0 mmol) of 1-amino-4,4-dimethoxybutane (3). The reaction mixture was stirred at room temperature for 12 h and the acetal of formula 4 precipitated from ether (100 ml). After cooling to 4° C. the crude acetal was collected by filtration and precipitated twice from methylene chloride by addition of ether to obtain 9.1 g of the acetal 4 as a white solid. The acetal was then dissolved in 50 ml of 0.1M HCL and stirred at room temperature for 4 h. The water was then removed under reduced pressure to give the aldehyde product of formula 5.

Scheme I

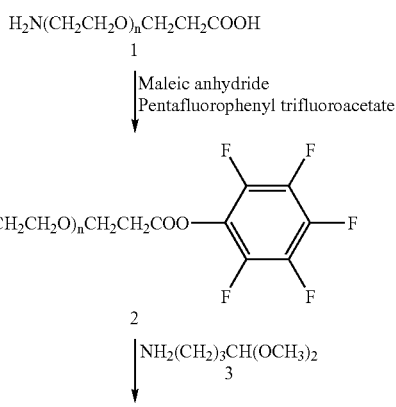

-continued

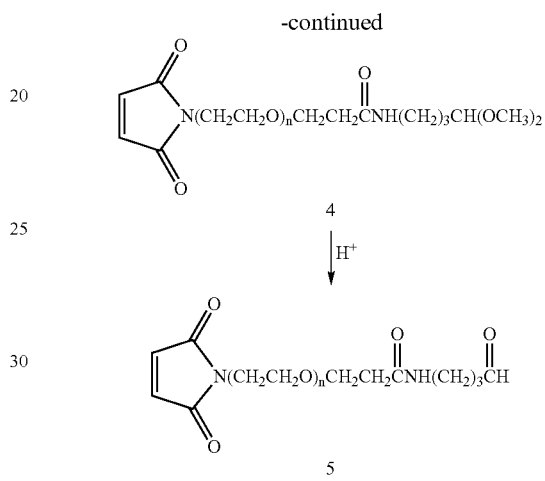

The integer n may be from about 11 to 2,300 but more preferably 11 to 1,000.

Example 10

Scheme I (Type IE-1)

Synthesis of PEG maleimido-amide Butyraldehyde

To 924 mg (3 mmol) of 6-maleimidocaproic acid pentafluorophenyl ester 1 (see Example 11) dissolved in dry methylene chloride (30 ml) was added 10 g (1 mmol) of alpha-amino-omega-carboxy-PEG (2) (MW 10,000, n=226) and 4-dimethylpyridine (402 mg, 3 mmol) dissolved in 50 ml of dry methylene chloride. The reaction mixture was stirred at room temperature for 2 h and the product precipitated in ether (100 ml). After cooling to 4° C. the crude amide of formula 3 was collected by filtration and precipitated twice from methylene chloride by addition of ether to give 9 g of compound 3 as a white solid.

To 10 g, (1 mmol) of polyethylene glycol acid 3, dissolved in dry methylene chloride (30 ml) was added dry and finely powdered NHS (0.56 g, 5 mmol). The flask was cooled in an ice-water bath and DCC (0.44 g, 2.16 mmol) added. The reaction mixture was stirred at 0° C. for 1 h and at room temperature for 24 h. The precipitated 1,3-dicyclohexylurea (DCU) was removed by filtration, and the filtrate added to ether (50 ml). After cooling to 4° C. the crude N-hydroxy succinimidyl ester was collected by filtration and purified by precipitating twice from methylene chloride by the addition of ether.

To the 9 g of the N-hydroxy ester derivative dissolved in dry methylene chloride (30 ml) there was added 1-amino-4,4-dimethoxybutane (4) (0.4 g, 2.5 mmol). The reaction mixture was stirred at room temperature for 2 h and the product precipitated in ether (100 ml) to give the acetal 5. After cooling to 4° C. the crude acetal of formula 5 was collected by filtration and precipitated twice from methylene chloride by addition of ether to give 8 g of compound 5 as a white solid. The acetal was then dissolved in 50 ml of 0.1M HCL and stirred at 4EC for one hour. The acid was neutralized with NaHCO$_3$ and the water removed under reduced pressure to give the amide-aldehyde 6 which was purified by chromatography.

(1 mmol) of •-amino-• hydroxy PEG (MW 10,000, n=226) dissolved in 50 ml of dry methylene chloride. The reaction mixture was stirred at room temperature for 2 h and the product precipitated in ether (100 ml). After cooling to 4° C. the crude amide of formula 3 was collected by filtration and precipitated twice from methylene chloride by addition of ether to give 9 g of compound 3 as a white solid.

To a solution of 606 mg (3 mmol) of 4-nitrophenyl chloroformate and 711.6 mg (5.82 mmol) of 4-dimethylaminopyridine dissolved in 10 ml of dry methylene chloride was added dropwise a solution of 9.7 g of the maleimide derivative 3 dissolved in 50 ml of methylene chloride and the solution stirred for 1 h at room temperature. The 4-nitro-

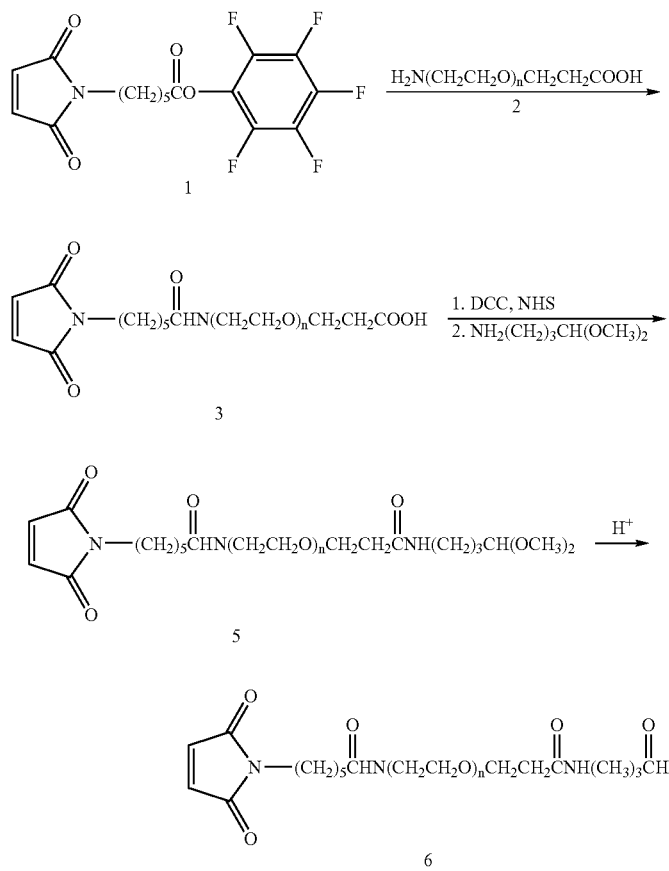

Scheme J

The integer n may be from about 11 to 2,300 but more preferably 11 to 1,000.

Example 11

Scheme K (Type IE-2)

Synthesis of PEG maleimido-urethane Butyraldehyde

Following the general procedure described by Adamczyk et al. (Org. Prep. Proc. Int. (1993) 25, 592) 6-aminocaproic acid was converted to pentafluorophenyl-6-maleimido-hexane-1-carboxylate 1. To 1.1 g (3 mmol) of compound 1 dissolved in dry methylene chloride (30 ml) was added 10 g phenyl carbonate derivative was not isolated but reacted directly with 519 mg (3.54 mmol) of 1-amino-4,4-dimethoxbutane (4). Stirring was continued for 20 h after which time the product 5 was precipitated by the addition of ether (100 ml).

By modifying the method of Huet et al., (Syn. 63, (1978), 10 g of the acetal 5 dissolved in 30 ml of methylene chloride was added to a mixture composed of 3 g of silica gel 60 and 0.3 g of a 10% aqueous oxalic acid solution. The resulting mixture was stirred at room temperature for one hour and NaHCO$_3$ added to neutralize the acid. The precipitated material was filtered with suction and the residue washed with a small amount of methylene chloride. Addition of ether to the filtrate afforded 9 g of the aldehyde 6.

Scheme K

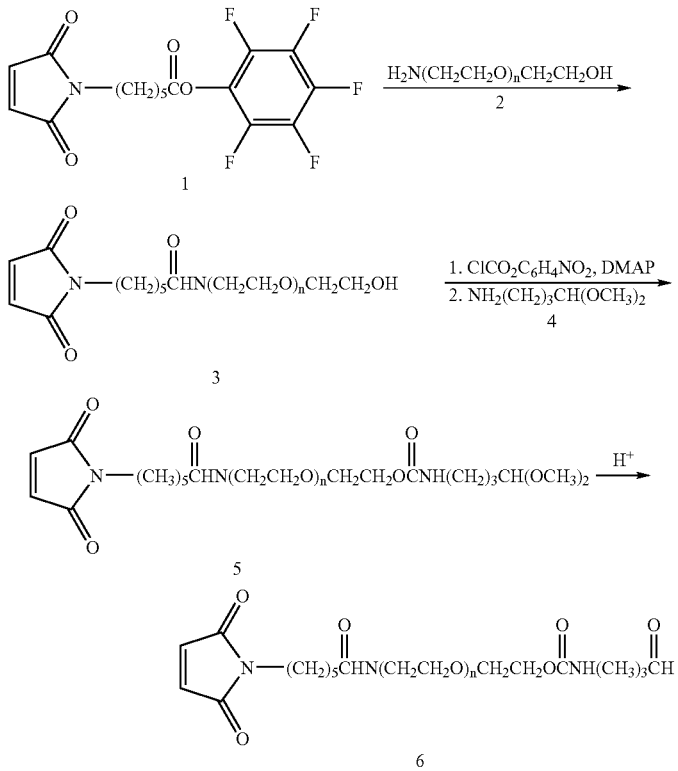

The integer n may be from about 11 to 2,300 but more preferably 11 to 1,000.

Example 12

Scheme L (Type 1G)

Synthesis of PEG Dimaleimide

To 981 mg (3 mmol) of pentafluorophenyl-6-maleimido-hexane-1-carboxylate (1) (Example 11) dissolved in dry methylene chloride (30 ml) was added 10 g (1 mmol) of •-amino-•-amino PEG (2) (MW 10,000, n=226) dissolved in 50 ml of dry methylene chloride. The reaction mixture was stirred at room temperature for 2 h and the product 3 obtained as a white powder by precipitation in ether (100 ml). The product was then dried under vacuum for 4 h.

Scheme L

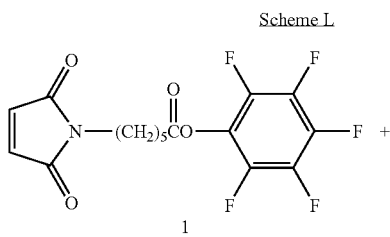

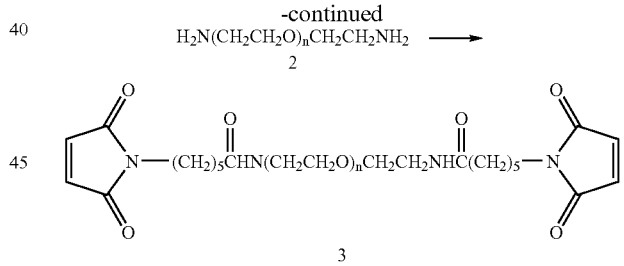

The integer n may be from about 11 to 2,300 but more preferably 11 to 1,000.

Example 13

Scheme M (Type 1H)

Synthesis of a-Substituted N-PEG Amino Acid

A mixture of pentane-1,2,5-triol of formula 1 (110.7 g, 97.5 mmol) and toluene-p-sulfonic acid (0.3 g) in acetone-light petroleum ether (bp 40–60) (1:1 60 ml) was refluxed 24 h with a Dean-Stark apparatus. The solvent was then removed under vacuum and the residue dissolved in ether. The ethereal solution was then washed with aqueous sodium carbonate, dried ($Na_2CO_3$) and the ether removed. The resulting oil was then distilled to give 10.7 g of 1,3 dioxolane-2,2-dimethyl-4-propanol of formula 2 bp. 117–118, 12 mm. (Golding et al., (1978) J. C. S. Perkin II, 839).

To a solution of compound 2 (10 g, 62.5 mmol) and triethylamine (12.65 g, 125 mmol) in 75 ml of dry CH$_2$Cl$_2$, was added slowly at –10EC, p-toluenesulfonyl chloride (17.8 g, 93.7 mmol). The mixture was stirred at room temperature for 12 hours, diluted with CHCl$_3$, and then washed successively with aq. dilute HCl and aq. NaHCO$_3$ (5%). The solution was dried (NaSO$_4$) and the solvent removed under reduced pressure. The residue was then chromatogaphed on silica gel using hexane-ethyl acetate (3:1) which afforded the pure tosylate 3 (19 g).

The sodium salt 4 was prepared by the reaction of sodium hydride and the benzylidene derivative of glycine methyl ester [for the alkylation of glycine derivatives see: a) O'Donnell et al., Tetrahedron Lett., 2641 (1978); b) Stork et al., J. Org. Chem. 41, 3491 (1976)]. To a solution of 4 (7.4 g, 42 mmol) in 80 ml of dry peroxide free tetrahydrofuran, was added 5 ml of hexamethyl phosphoramide followed by the slow addition of the tosylate 2 (13.2 g, 42 mmol) dissolved in 20 ml of dry tetrahydrofuran. The reaction was allowed to proceed for twelve hours at room temperature, poured into ice water and extracted with CH$_2$Cl$_2$. The organic layer was dried (MgSO$_4$) and the solvent removed under reduced pressure to give crude 5. Hydrolyses of 5 with 1N HCl at room temperature for one hour afforded the amino ester 6. Compound 6 was then treated with triethylamine (2 eq)/H$_2$O for 24 hours at room temperature to give the amino acid 7. Compound 7 was purified by ion exchange chromatography [Dowex 1 (OH-form) and 50W (H-form)] to give 6 g of pure product.

To a solution of the glycine derivative 7 (250 mg, 1.4 mmol) dissolved in 25 mL of water at pH 8–8.2 was added slowly mPEG p-nitrophenyl carbonate 8 (14 g, 1.4 mmol, MW 10,000) over one hour while maintaining the pH at 8.2 with 0.2N NaOH (for the preparation of 8 see Monfardini et al., Bioconjugate Chem. (1995) 6, 62). After being stirred for four hours, the solution was cooled to OEC and acidified to pH 2.5 with 1N HCl. The mixture was extracted with ether, the ether discarded and the product extracted three times with chloroform. The chloroform solution was dried, concentrated, and then slowly added to ether. The precipitate was collected and the product 9 crystallized from absolute ethanol.

To the glycine derivative 9 (3 g, 0.3 mmol) dissolved in 40 mL was added NaIO$_4$ (160 mg, 0.75 mmol) and the reaction allowed to proceed for one hour in the dark. Excess periodate was destroyed by the addition of 2 mL of ethylene glycol and the aldehyde 10 purified on a Sephadex G 10 column.

Scheme H

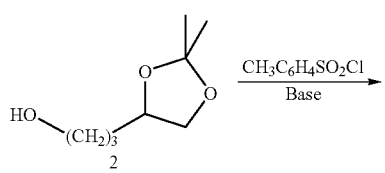

-continued

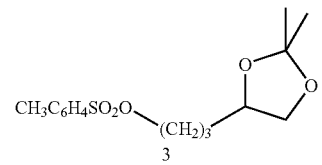

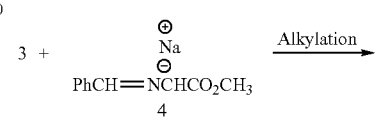

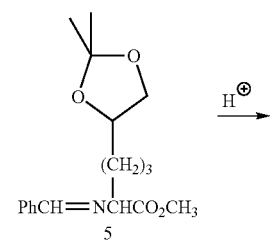

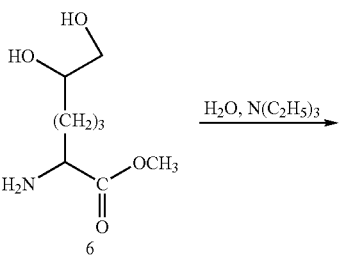

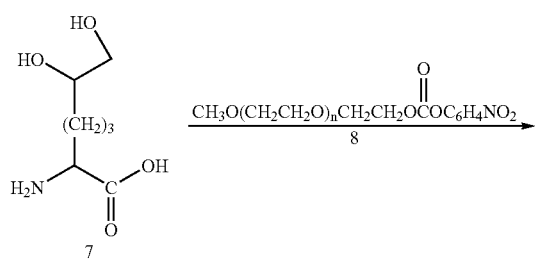

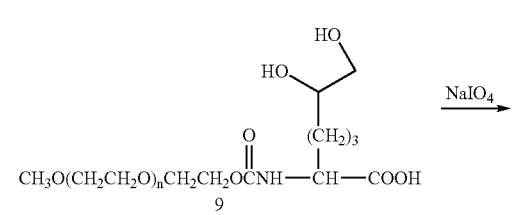

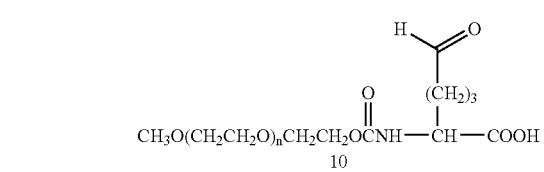

The integer n may be from about 11 to 2,300 but more preferably 11 to 1,000.

What is claimed:

1. An aldehyde having the formula:

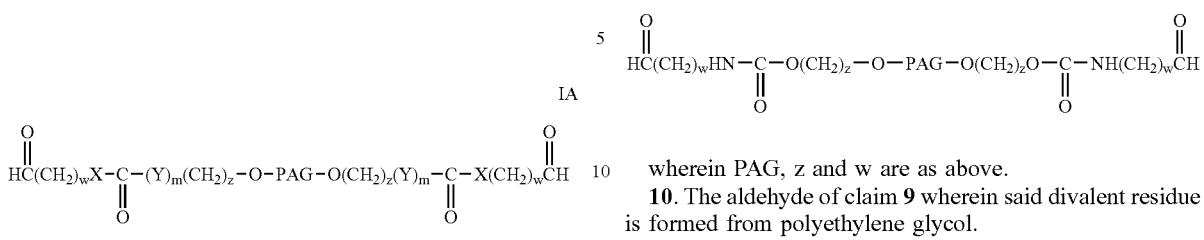

IA wherein X and Y are individually selected from —O— or —NH— with the proviso that X is NH when m is 1 and Y is —O—, PAG is a divalent residue of polyalkylene glycol resulting from removal of the terminal hydroxy groups and having a molecular weight of from about 500 to about 100,000 Daltons, z is an integer of from 2 to 4, m is an integer of from 0 to 1, and w is an integer of from 2 to 8, wherein the aldehyde group is free or protected with a hydrolyzable aldehyde protecting group.

2. The aldehyde of claim 1 wherein said residue is formed from polyethylene glycol.

3. The aldehyde of claim 2 wherein the residue has a molecular weight of 5,000 to 50,000 Daltons.

4. The aldehyde of claim 1 wherein said aldehyde has a formula:

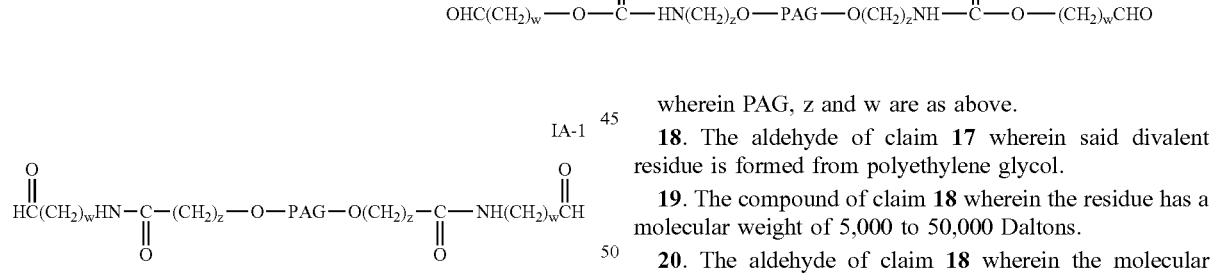

wherein PAG, z, and w are as above.

5. The aldehyde of claim 4 wherein said divalent residue is polyethylene glycol.

6. The aldehyde of claim 5 wherein the residue has a molecular weight of 5,000 to 50,000 Daltons.

7. The aldehyde of claim 5 wherein the molecular weight of the residue is about 10,000 Daltons.

8. The aldehyde of claim 5 wherein the molecular weight of the residue is about 20,000 Daltons.

9. The aldehyde of claim 1 wherein said aldehyde has a formula:

IA-2

$$HC(CH_2)_wHN-\underset{\underset{O}{\|}}{C}-O(CH_2)_z-O-PAG-O(CH_2)_zO-\underset{\underset{O}{\|}}{C}-NH(CH_2)_wCH$$

wherein PAG, z and w are as above.

10. The aldehyde of claim 9 wherein said divalent residue is formed from polyethylene glycol.

11. The aldehyde of claim 10 wherein the residue has a molecular weight of 5,000 to 50,000 Daltons.

12. The aldehyde of claim 10 wherein the said residue has a molecular weight of 20,000 Daltons.

13. The aldehyde of claim 1 having the formula:

IA-3

$$OHC(CH_2)_w-HN-\underset{\underset{}{\overset{O}{\|}}}{C}-HN(CH_2)_zO-PAG-O(CH_2)_zNH-$$
$$-\underset{\underset{}{\overset{O}{\|}}}{C}-NH-(CH_2)_wCHO$$

wherein PAG, z and w are as above.

14. The compound of claim 13 wherein said divalent residue is polyethylene glycol.

15. The compound of claim 14 wherein the residue has a molecular weight of 5,000 to 50,000 Daltons.

16. The aldehyde of claim 14 wherein the molecular weight of the residue is 20,000 Daltons.

17. The aldehyde of claim 1 having the formula:

IA-4

$$OHC(CH_2)_w-O-\underset{\underset{}{\overset{O}{\|}}}{C}-HN(CH_2)_zO-PAG-O(CH_2)_zNH-\underset{\underset{}{\overset{O}{\|}}}{C}-O-(CH_2)_wCHO$$

wherein PAG, z and w are as above.

18. The aldehyde of claim 17 wherein said divalent residue is formed from polyethylene glycol.

19. The compound of claim 18 wherein the residue has a molecular weight of 5,000 to 50,000 Daltons.

20. The aldehyde of claim 18 wherein the molecular weight of the residue is 20,000 Daltons.

21. An aldehyde of the formula:

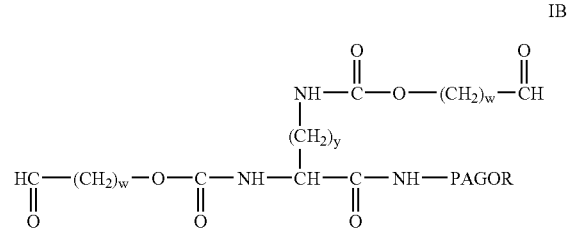

IB wherein R is hydrogen or lower alkyl, w is an integer from 2 to 8, y is an integer of from 2 to 4, and PAG is a divalent residue of polyalkylene glycol resulting from removal of the terminal hydroxy groups and having a molecular weight of from about 500 to about 100,000 Daltons.

22. The aldehyde of claim 21 wherein PAG is formed from polyethylene glycol having a molecular weight of from 5,000 to 50,000 Daltons.

23. The aldehyde of claim 22 where R is methyl and the PEG residue has a molecular weight of about 10,000 Daltons.

24. The aldehyde of claim 22 wherein R is methyl and the PEG residue has a molecular weight of 20,000 Daltons.

* * * * *